United States Patent
Fujii et al.

(10) Patent No.: US 6,930,115 B2
(45) Date of Patent: Aug. 16, 2005

(54) ANTITUMOR EFFECT POTENTIATORS

(75) Inventors: Akihiro Fujii, Tokyo (JP); Hiroshi Tanaka, Tokyo (JP); Makio Otsuki, Tokyo (JP); Takafumi Kawaguchi, Tokyo (JP); Kouichi Oshita, Tokyo (JP)

(73) Assignee: Mitsubishi Pharma Corporation, Osaka (JP)

( * ) Notice: Subject to any disclaimer, the term of this patent is extended or adjusted under 35 U.S.C. 154(b) by 49 days.

(21) Appl. No.: 10/311,928

(22) PCT Filed: Jun. 22, 2001

(86) PCT No.: PCT/JP01/05377

§ 371 (c)(1),
(2), (4) Date: Feb. 5, 2003

(87) PCT Pub. No.: WO01/97849

PCT Pub. Date: Dec. 27, 2001

(65) Prior Publication Data

US 2003/0165576 A1 Sep. 4, 2003

(30) Foreign Application Priority Data

Jun. 23, 2000 (JP) ........................................ 2000-190233

(51) Int. Cl.$^7$ .................. A61K 31/437; A61K 31/4409
(52) U.S. Cl. ...................................... 514/300; 514/357
(58) Field of Search ................................ 514/300, 357

(56) References Cited

U.S. PATENT DOCUMENTS 5,906,819 A   5/1999   Kaibuchi et al. .......... 424/94.5

FOREIGN PATENT DOCUMENTS

| EP | 0 956 865 | 11/1999 |
|---|---|---|
| EP | 1 064 944 | 1/2001 |
| EP | 1064944 | 1/2001 |
| EP | 1 177 796 | 2/2002 |
| JP | 8-268965 | 10/1996 |
| JP | 10-113187 | 5/1998 |
| JP | 10-201480 | 8/1998 |
| JP | 00/64478 | 11/2000 |
| WO | 97/40835 | 11/1997 |
| WO | 98/06433 | 2/1998 |
| WO | 00/64478 | 11/2000 |

OTHER PUBLICATIONS

A. V. Somlyo et al., "Rho–Kinase Inhibitor Retards Migration and in vivo Dissemination of Human Prostate Cancer Cells", Biochem. Biophys. Res. Commun., Mar. 2000, vol. 269, pp. 652–659.
K. Itoh et al., "An Essential Part for Rho–Associated Kinase in the Transcellular Invasion of Tumor Cells", Nat. Med., 1999, vol. 5, No. 2, pp. 221–225.
T. Saito, 11. Tazai Heiyouhou. Gairon, Oct., 1988, Nippon Rinsho, No. 46 (1988, supplemental issue), pp. 254–258.
MEDLINE Abstract of Somlyo reference (Biochem. Biophys. Res. Commun., Mar. 2000, vol. 269, pp. 652–659).
MEDLINE Abstract of Itoh reference (Nat. Med., 1999, vol. 5, No. 2, pp. 221–225).
Saito reference (Nippon Rinsho, 1988, No. 46, pp. 254–258, "Cancer Therapy Manual", this publication describes the outline of multidrug regimen in cancer chemotherapy).

*Primary Examiner*—Bernard Dentz
(74) *Attorney, Agent, or Firm*—Wenderoth, Lind & Ponack L.L.P.

(57) ABSTRACT

When used concurrently with an antitumor agent, a compound having a Rho kinase inhibitory activity, such as (R)-(+)-N-(4-pyridyl)-4-(1-aminoethyl)benzamide, reinforces an antitumor effect of the antitumor agent and is useful as an antitumor effect potentiator.

Particularly, a compound having a Rho kinase inhibitory activity used with an antitumor agent in combination can reduce the dose of the antitumor agent, which in turn affords provision of a sufficient effect and/or reduction of side effects.

10 Claims, No Drawings

ANTITUMOR EFFECT POTENTIATORS

This application is a U.S. national stage of International Application No. PCT/JP01/05377 filed Jun. 22, 2001.

TECHNICAL FIELD

The present invention relates to an antitumor effect potentiator containing a compound having a Rho kinase inhibitory activity as an active ingredient, which potentiates antitumor effect shown by antitumor agents.

BACKGROUND ART

For treatment of malignant tumor, surgical therapy, chemotherapy, radiation therapy and the like are available. The treatment methods have certainly been improved in recent years due to the development of pharmaceutical agents used for chemotherapy, advanced surgical techniques and the like. For administration of antitumor agents, a single administration method (continuous, intermittent, large amount in short period), multidrug combination administration method, complex administration method with operation radiation therapy, topical administration method (tumor perfusion method, intraarterial administration method, intrabody cavity administration method), systemic administration method and the like are available. The administration of antitumor agents is based on location of primary cancer, sensitivity to pharmaceutical agents, presence or absence of metastasis, action mechanism of antitumor agents and the like and individual complex treatment methods for each cancer have been considered.

In general, however, the problem of side effects is inseparable in the treatment of malignant tumor with antitumor agents.

For example, bone marrow toxicity such as decrease in hematopoietic stem cells·bone marrow hypoplasia and the like, gastrointestinal tract toxicity and the like caused by alkylating agents, bone marrow toxicity, gastrointestinal tract toxicity, hepatopathy and the like caused by antimetabolite, cardiotoxicity, hemotoxicity, pulmonary toxicity (pulmonary fibrosis) and the like caused by anticancer antibiotic, neurotoxicity, bone marrow toxicity and the like caused by plant-derived anticancer agent, renal disorder, gastrointestinal tract toxicity and the like caused by platinum complex compound (particularly, nephrotoxicity is feared with regard to cisplatin, which is dealt with by intake of a large amount of water to reduce damage on kidney) are representative side effects.

When acute side effects occur, such as strong nausea, vomitus, diarrhea, allergy reaction, stomatitis, fever (40° C. or above), tachycardia·arrhythmia and hypotension, the dose of antitumor agents is reduced or the administration is interrupted. When chronical side effect and/or organ disorders such as myelopathia, severe infectious diseases, hepatopathy, hypofibrinogenemia, abnormal finding in lung, indication of cardiac failure, renal disorder and nervous symptom appear, administration of antitumor agents is completely stopped.

As mentioned above, these side effects are the factors limiting the dose of antitumor agents and pose serious issues, because side effects force reduction of dose and discontinuation of medication despite the effect provided by the agents.

While concurrent use of antitumor agents for the treatment of malignant tumor is one of the therapies employed, the combined use of the existing antitumor agents generally causes side effects such as potentiation of bone marrow suppression and the like. Therefore, strict attention to the dose, such as reduction of dose while continuously monitoring the condition of patients and the like becomes warranted. The combination of particular antitumor agents, too, is associated with the problem of side effects as in the case of single administration, because side effects that require particularly careful handling appear, such as cardiotoxicity by the combination of cyclophosphamide or ifosfamide and pentostatin, myelopathia by the combination of fluorouracil drug and sorivudine (antivirus agent), nervous disorder by the combination of vinca alkaloid pharmaceutical agent and platinum complex compound, and respiratory disorder by the combination of vinca alkaloid drug and mitomycin C.

With the aim of potentiation of antitumor effect and reduction of side effects, administration of different pharmaceutical agents having an effect on the antitumor agent before and after administration of antitumor agents and during administration thereof has been tried in recent years (e.g., fluorouracil and leucovorin, fluorouracil and thymidine, combination drug (UFT) of tegafur and uracil, administration of methotrexate prior to administration of fluorouracil and the like).

However, these attempts have not provided a sufficient treatment effect on malignant tumor.

In contrast, it has been clarified that Rho is activated upon receipt of signals from various cell membrane receptors, and the activated Rho functions via actomyosin system as a molecular switch of various cellular phenomena, such as smooth muscle constriction, cell motility, cell adhesion, morphological changes in the cell, cell growth and the like. Moreover, an important role played by Rho kinase, which is present in the downstream of the signal transduction pathway via Rho, in the above-mentioned responsive cell phenomena by Rho is being clarified.

In addition, a compound of the formula (I) to be mentioned later has been recently reported (WO98/06433) as a compound having a Rho kinase inhibitory activity. Certain isoquinolinesulfonamide derivative and isoquinoline derivative are also reported to show a Rho kinase inhibitory activity (WO98/06433 and Naunyn-Schmiedeberg's Archives of Pharmacology 385(1) Suppl., R219, 1998). Furthermore, it has been reported that ethacrynic acid, certain vinyl benzene derivatives such as 4-[2-(2,3,4,5,6-pentafluorophenyl)-acryloyl]cinnamic acid and the like and cinnamic acid derivative have a Rho kinase inhibitory activity (WO00/57914, JP-A-2000-44513).

The pharmaceutical use of a compound having a Rho kinase inhibitory activity is disclosed in WO98/06433, and described to be extensively useful as a therapeutic agent of hypertension, a therapeutic agent of angina pectoris, a cerebrovascular spasm suppressant, a therapeutic agent of asthma, a therapeutic agent of peripheral circulatory disturbance, a premature delivery preventive, a therapeutic agent of arterial sclerosis, an anticancer drug, an anti-inflammatory agent, an immunosuppressant, a therapeutic agent of autoimmune diseases, an anti-AIDS agent, a therapeutic agent of osteoporosis, a therapeutic agent of retinopathy, a cerebral function improver, a contraceptive drug, and a gastrointestinal tract infection preventive.

Furthermore, the compound of formula (I) has been already known to be useful as an agent for the prophylaxis or treatment of disorders of circulatory organs, such as coronary, cerebral, renal, peripheral artery and the like (e.g., a therapeutic agent of hypertension, a therapeutic agent of angina pectoris, a therapeutic agent of renal and peripheral circulation disorder, a suppressive agent of cerebrovascular contraction and the like), which is potent and long lasting, and also as a therapeutic agent of asthma (JP-A-62-89679, JP-A-3-218356, JP-A-4-273821, JP-A-5-194401, JP-A-6-41080 and WO95/28387).

The isoquinolinesulfonamide derivative described in the above-mentioned WO98/06433 is known to be effective as a vasodilating agent, a therapeutic agent of hypertension, a cerebral function improver, an anti-asthma agent, a heart protecting agent, a platelet aggregation inhibitor, a therapeutic agent of neurologic manifestation, an anti-inflammatory agent, an agent for the prevention and treatment of hyperviscosity syndrome, a therapeutic agent of glaucoma, a diminished tension agent, a motor paralysis improver of cerebral thrombosis, an agent for prevention and treatment of virus infection and transcriptional control factor inhibitor (JP-A-57-200366, JP-A-61-227581, JP-A-2-256617, JP-A-4-264030, JP-A-6-56668, JP-A-6-80569, JP-A-6-293643, JP-A-7-41424, JP-A-7-277979, WO97/23222, JP-A-9-227381, JP-A-10-45598 and JP-A-10-87491).

Moreover, the isoquinoline derivative described in the above-mentioned publication (Naunyn-Schmiedeberg's Archives of Pharmacology 385(1) Suppl., R219, 1998) is known to be useful as an agent for the prevention or treatment of brain tissue disorder due to vasospasm (WO97/28130).

From the foregoing, it has been clarified that Rho and Rho kinase are involved in the formation of tumor and induction of infiltration and metastasis of cancer cells, and that a compound having a Rho kinase inhibitory activity is useful as an antitumor agent.

However, there has been no report on potentiation of the antitumor effect of different antitumor agents by a compound having a Rho kinase inhibitory activity.

DISCLOSURE OF THE INVENTION

The present invention aims at solving the above-mentioned problems and its object is to provide an antitumor effect potentiator that can reinforce the antitumor effect of an antitumor agent, can be co-used with an antitumor agent, can educe the dose, can provide a sufficient effect and/or reduce side effects.

As a result of intensive studies in an attempt to solve the above-mentioned problems, the present inventors have found that a compound having a Rho kinase inhibitory activity reinforces the antitumor effect of an antitumor agent and is useful as an antitumor effect potentiator, which resulted in the completion of the present invention.

Therefore, a compound having a Rho kinase inhibitory activity of the present invention when used with an antitumor agent in combination can reduce the dose of antitumor agents, and can provide a sufficient effect and/or reduce side effects.

Accordingly, the present invention provides the following.

(1) An antitumor effect potentiator comprising a compound having a Rho kinase inhibitory activity as an active ingredient, which reinforces an antitumor effect of an antitumor agent.

(2) The antitumor effect potentiator of (1) above, wherein the compound having a Rho kinase inhibitory activity is an amide compound of the following formula (I)

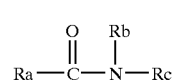

wherein

Ra is a group of the formula

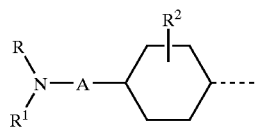

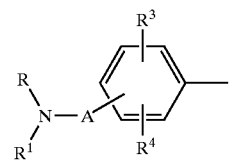

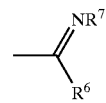

in the formulas (a) and (b),

R is hydrogen, alkyl, or cycloalkyl, cycloalkylalkyl, phenyl or aralkyl, which optionally has a substituent on the ring, or a group of the formula

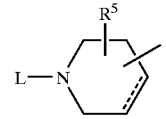

wherein $R^6$ is hydrogen, alkyl or formula:—$NR^8R^9$ wherein $R^8$ and $R^9$ are the same or different and each is hydrogen, alkyl, aralkyl or phenyl, $R^7$ is hydrogen, alkyl, aralkyl, phenyl, nitro or cyano, or $R^6$ and $R^7$ in combination show a group forming a heterocycle optionally further having, in the ring, oxygen atom, sulfur atom or optionally substituted nitrogen atom, $R^1$ is hydrogen, alkyl, or cycloalkyl, cycloalkylalkyl, phenyl or aralkyl, which optionally has a substituent on the ring, or R and $R^1$ in combination form, together with the adjacent nitrogen atom, a group forming a heterocycle optionally further having, in the ring, oxygen atom, sulfur atom or optionally substituted nitrogen atom, $R^2$ is hydrogen or alkyl, $R^3$ and $R^4$ are the same or different and each is hydrogen, alkyl, aralkyl, halogen, nitro, amino, alkylamino, acylamino, hydroxy, alkoxy, aralkyloxy, cyano, acyl, mercapto, alkylthio, aralkylthio, carboxy, alkoxycarbonyl, carbamoyl, mono- or dialkylcarbamoyl or azide, and A is a group of the formula

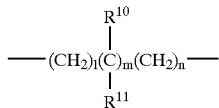
(e)

wherein $R^{10}$ and $R^{11}$ are the same or different and each is hydrogen, alkyl, haloalkyl, aralkyl, hydroxyalkyl, carboxy or alkoxycarbonyl, or $R^{10}$ and $R^{11}$ show a group which forms cycloalkyl in combination and l, m and n are each 0 or an integer of 1–3, in the formula (c), L is hydrogen, alkyl, aminoalkyl, mono- or dialkylaminoalkyl, tetrahydrofurfuryl, carbamoylalkyl, phthalimidoalkyl, amidino or a group of the formula

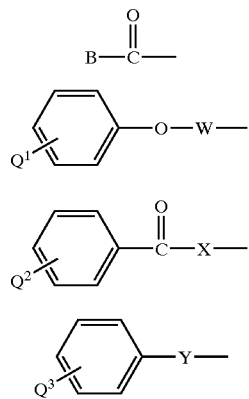

(f)

(g)

(h)

(i)

wherein B is hydrogen, alkyl, alkoxy, aralkyl, aralkyloxy, aminoalkyl, hydroxyalkyl, alkanoyloxyalkyl, alkoxycarbonylalkyl, α-aminobenzyl, furyl, pyridyl, phenyl, phenylamino, styryl or imidazopyridyl, $Q^1$ is hydrogen, halogen, hydroxy, aralkyloxy or thienylmethyl, W is alkylene, $Q^2$ is hydrogen, halogen, hydroxy or aralkyloxy, X is alkylene, $Q^3$ is hydrogen, halogen, hydroxy, alkoxy, nitro, amino, 2,3-dihydrofuryl or 5-methyl-3-oxo-2,3,4,5-tetrahydropyridazin-6-yl;

and Y is a single bond, alkylene or alkenylene, and in the formula (c), a broken line is a single bond or a double bond, and $R^5$ is hydrogen, hydroxy, alkoxy, alkoxycarbonyloxy, alkanoyloxy or aralkyloxycarbonyloxy;

Rb is a hydrogen, an alkyl, an aralkyl, an aminoalkyl or a mono- or dialkylaminoalkyl; and Rc is an optionally substituted heterocycle containing nitrogen, an isomer thereof and/or a pharmaceutically acceptable acid addition salt thereof.

(3) The antitumor effect potentiator of (1) above, wherein the compound having a Rho kinase inhibitory activity is an amide compound of the following formula (I')

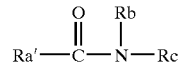
(I')

wherein

Ra' is a group of the formula

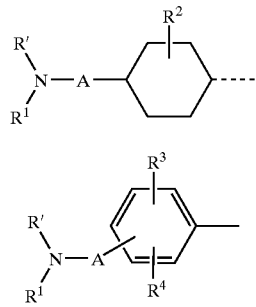

(a')

(b')

wherein

R' is hydrogen, alkyl, or cycloalkyl, cycloalkylalkyl, phenyl or aralkyl, which optionally has a substituent on the ring, $R^1$ is hydrogen, alkyl, or cycloalkyl, cycloalkylalkyl, phenyl or aralkyl, which optionally has a substituent on the ring, or R' and $R^1$ in combination form, together with the adjacent nitrogen atom, a group forming a heterocycle optionally further having, in the ring, oxygen atom, sulfur atom or optionally substituted nitrogen atom, $R^2$ is hydrogen or alkyl, $R^3$ and $R^4$ are the same or different and each is hydrogen, alkyl, aralkyl, halogen, nitro, amino, alkylamino, acylamino, hydroxy, alkoxy, aralkyloxy, cyano, acyl, mercapto, alkylthio, aralkylthio, carboxy, alkoxycarbonyl, carbamoyl, mono- or dialkylcarbamoyl or azide, and A is a group of the formula

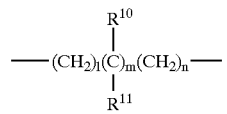
(e)

wherein $R^{10}$ and $R^{11}$ are the same or different and each is hydrogen, alkyl, haloalkyl, aralkyl, hydroxyalkyl, carboxy or alkoxycarbonyl, or $R^{10}$ and $R^{11}$ show a group which forms cycloalkyl in combination and l, m and n are each 0 or an integer of 1–3, Rb is a hydrogen, an alkyl, an aralkyl, an aminoalkyl or a mono- or dialkylaminoalkyl; and Rc is an optionally substituted heterocycle containing nitrogen, an isomer thereof and/or a pharmaceutically acceptable acid addition salt thereof.

(4) The antitumor effect potentiator of (1) above, wherein the compound having a Rho kinase inhibitory activity is a compound selected from the group consisting of (+)-trans-4-(1-aminoethyl)-1-(4-pyridylcarbamoyl) cyclohexane, (+)-trans-N-(1H-pyrrolo[2,3-b]pyridin-4- yl)-4-(1-aminoethyl)cyclohexanecarboxamide, (R)-(+)-N-(4-pyridyl)-4-(1-aminoethyl)benzamide and (R)-(+)-N-(1H-pyrrolo[2,3-b]pyridin-4-yl)-4-(1-aminoethyl)benzamide, and/or a pharmaceutically acceptable acid addition salt thereof, particularly (R)-(+)-N-(4-pyridyl)-4-(1-aminoethyl)benzamide and/or a pharmaceutically acceptable acid addition salt thereof.

(5) The antitumor effect potentiator of the above-mentioned (1) or (2), wherein the antitumor agent is selected from cisplatin, etoposide and paclitaxel, particularly cisplatin.

(6) A pharmaceutical composition for potentiation of antitumor effect, which comprises a compound having a Rho kinase inhibitory activity and a pharmaceutically acceptable carrier, which reinforces an antitumor effect of an antitumor agent.

(7) The pharmaceutical composition for potentiation of antitumor effect of (6) above, wherein the compound having a Rho kinase inhibitory activity is an amide compound of the formula (I), particularly the formula (I'), an isomer thereof and/or a pharmaceutically acceptable acid addition salt thereof.

(8) The pharmaceutical composition for potentiation of antitumor effect of (6) above, wherein the compound having a Rho kinase inhibitory activity is a compound selected from the group consisting of (+)-trans-4-(1-aminoethyl)-1-(4-pyridylcarbamoyl)cyclohexane, (+)-trans-N-(1H-pyrrolo[2,3-b]pyridin-4-yl)-4-(1-aminoethyl)cyclohexanecarboxamide, (R)-(+)-N-(4-pyridyl)-4-(1-aminoethyl)benzamide and (R)-(+)-N-(1H-pyrrolo[2,3-b]pyridin-4-yl)-4-(1-aminoethyl)benzamide, and/or a pharmaceutically acceptable acid addition salt thereof, particularly (R)-(+)-N-(4-pyridyl)-4-(1-aminoethyl)benzamide and/or a pharmaceutically acceptable acid addition salt thereof.

(9) The pharmaceutical composition for potentiation of antitumor effect of the above-mentioned (6) or (7), wherein the antitumor agent is selected from cisplatin, etoposide and paclitaxel, particularly cisplatin.

(10) A pharmaceutical composition for the treatment of tumor, which comprises a compound having a Rho kinase inhibitory activity, an antitumor agent and a pharmaceutically acceptable carrier.

(11) The pharmaceutical composition for treatment of tumor of (10) above, wherein the compound having a Rho kinase inhibitory activity is an amide compound of the formula (I), particularly the formula (I'), an isomer thereof and/or a pharmaceutically acceptable acid addition salt thereof.

(12) The pharmaceutical composition for treatment of tumor of (10) above, wherein the compound having a Rho kinase inhibitory activity is a compound selected from the group consisting of (+)-trans-4-(1-aminoethyl)-1-(4-pyridylcarbamoyl)cyclohexane, (+)-trans-N-(1H-pyrrolo[2,3-b]pyridin-4-yl)-4-(1-aminoethyl)cyclohexanecarboxamide, (R)-(+)-N-(4-pyridyl)-4-(1-aminoethyl)benzamide and (R)-(+)-N-(1H-pyrrolo[2,3-b]pyridin-4-yl)-4-(1-aminoethyl)benzamide, and/or a pharmaceutically acceptable acid addition salt thereof, particularly (R)-(+)-N-(4-pyridyl)-4-(1-aminoethyl)benzamide and/or a pharmaceutically acceptable acid addition salt thereof.

(13) The pharmaceutical composition for treatment of tumor of (10) or (11) above, wherein the antitumor agent is selected from cisplatin, etoposide and paclitaxel, particularly cisplatin.

(14) A method of treating a tumor, which comprises administering a pharmaceutically effective amount of a compound having a Rho kinase inhibitory activity and a pharmaceutically effective amount of an antitumor agent to a patient.

(15) The method of (14) above, wherein the compound having a Rho kinase inhibitory activity is an amide compound of the formula (I), particularly the formula (I'), an isomer thereof and/or a pharmaceutically acceptable acid addition salt thereof.

(16) The method of (14) above, wherein the compound having a Rho kinase inhibitory activity is a compound selected from the group consisting of (+)-trans-4-(1-aminoethyl)-1-(4-pyridylcarbamoyl)cyclohexane, (+)-trans-N-(1H-pyrrolo[2,3-b]pyridin-4-yl)-4-(1-aminoethyl)cyclohexanecarboxamide, (R)-(+)-N-(4-pyridyl)-4-(1-aminoethyl)benzamide and (R)-(+)-N-(1H-pyrrolo[2,3-b]pyridin-4-yl)-4-(1-aminoethyl)benzamide, and/or a pharmaceutically acceptable acid addition salt thereof, particularly (R)-(+)-N-(4-pyridyl)-4-(1-aminoethyl)benzamide and/or a pharmaceutically acceptable acid addition salt thereof.

(17) The method of the above-mentioned (14) or (15), wherein the antitumor agent is selected from cisplatin, etoposide and paclitaxel, particularly cisplatin.

(18) Use of a compound having a Rho kinase inhibitory activity for the production of an antitumor effect potentiator that reinforces an antitumor effect of an antitumor agent.

(19) The use of (18) above, wherein the compound having a Rho kinase inhibitory activity is an amide compound of the formula (I), particularly the formula (I'), an isomer thereof and/or a pharmaceutically acceptable acid addition salt thereof.

(20) The use of (18) above, wherein the compound having a Rho kinase inhibitory activity is a compound selected from the group consisting of (+)-trans-4-(1-aminoethyl)-1-(4-pyridylcarbamoyl)cyclohexane, (+)-trans-N-(1H-pyrrolo[2,3-b]pyridin-4-yl)-4-(1-aminoethyl)cyclohexanecarboxamide, (R)-(+)-N-(4-pyridyl)-4-(1-aminoethyl)benzamide and (R)-(+)-N-(1H-pyrrolo[2,3-b]pyridin-4-yl)-4-(1-aminoethyl)benzamide, and/or a pharmaceutically acceptable acid addition salt thereof, particularly (R)-(+)-N-(4-pyridyl)-4-(1-aminoethyl)benzamide and/or a pharmaceutically acceptable acid addition salt thereof.

(21) The use of the above-mentioned (18) or (19), wherein the antitumor agent is selected from cisplatin, etoposide and paclitaxel, particularly cisplatin.

(22) A commercial package comprising the pharmaceutical composition for potentiation of antitumor effect of any of the above-mentioned (6)–(9) and a written matter associated therewith, the written matter stating that the pharmaceutical composition can or should be used for reinforcing an antitumor effect of an antitumor agent.

(23) A commercial package comprising the pharmaceutical composition for treatment of tumor of any of the above-mentioned (10)–(13) and a written matter associated therewith, the written matter stating that the pharmaceutical composition can or should be used for treatment of tumor.

DETAILED DESCRIPTION OF THE INVENTION

In the present invention, the "antitumor agent" may have any mechanism as long as it acts on tumor, particularly malignant tumor, and aids clinical remission of the cancer disease. In addition to those conventionally used in the pertinent field, any clinically applicable one inclusive of those under development and those to be developed from now can be the target of the reinforcing action of the antitumor effect potentiator and the pharmaceutical composition for reinforcing an antitumor effect of the present invention. More specifically, it is the anticancer agent to be mentioned below (Examples). Specific examples of the antitumor agent include alkylating agent (chlormethine, nitrogen mustard N-oxide hydrochloride, inproquone, triaziquone, melphalan, chlorambucil, cyclophosphamide, ifosfamide, trofosfamide, mannomustine, estramustine sodium phosphate, busulphan, improsulfan tosilate, dacarbazine, procarbazine hydrochloride, carbazilquinone, triethylenemelamine, thiotepa, mitobronitol, carmustine (BCNU), lomustine (CCNU), methyl-CCNU, nimustine hydrochloride (ACNU), streptozotocin, TA-077, dacarbazine, pipobroman, uramustine, epipropidine and the like), antimetabolite (methotrexate, hydroxyurea, aminopterin, leucovorin calcium, fluorouracil, tegafur, tegafur uracil combination drug, S-1, carmofur, doxifluridine, FUDR, cytarabine, cytarabine ocphosphate, ancitabine, enocitabine, 6-mercaptopurine riboside, mercaptopurine, 8-azaguanine, tabloid, azacytidine, gemcitabine and the like), anticancer antibiotic (doxorubicin hydrochloride, daunorubicin hydrochloride, aclarubicin hydrochloride, idarubicin hydrochloride, epirubicin hydrochloride, pirarubicin hydrochlide, 4'-epidoxorubicin, 4'-O-tetrahydropyranyl adriamycin, bleomycin, peplomycin sulfate, mitomycin C, actinomycin C, actinomycin D, chromomycin $A_3$, mithramycin, neocarzinostatin, zinostatin stimalamer, sarkomycin, carzinophilin and the like), plant-derived anticancer agent (vincristine sulfate, vinblastine sulfate, vindesine sulfate, podophyllotoxin, etoposide, teniposide, irinotecan hydrochloride, demecolcin, paclitaxel, docetaxel hydrate and the like), platinum complex compound (cisplatin, carboplatin, nedaplatin and the like), hormone drug (prednisolone, prednisone, dexamethasone, cortisone acetate, hydrocortisone, betamethasone, mitotane, aminoglutethimide, methyltestosterone, testosterone propionate, testosterone enanthate, fluoxymesterone, dromostanolone propionate, testolactone, calusterone, conjugated estrogen, ethynylestradiol, diethylstilbestrol phosphate, diethylstilbestrol, hexestrol, chlorotrianisene, epitiostanol, mepitiostane, tamoxifen citrate, nafoxidine hydrochloride, citric acid clomiphene, toremifene citrate, hydroxyprogesterone caproate, medroxyprogesterone acetate, megestrol acetate, chlormadinone acetate, cyproterone acetate, norethisterone, allylestrenol, dried thyroid, levothyroxine sodium, liothyronine sodium, alprostadil, goserelin acetate, leuprorelin acetate, flutamide and the like), other antitumor agents (mitoxantrone hydrochloride, aceglatone, etoglucide, L-asparaginase, fadrozole hydrochloride hydrate, sobuzoxane, pentostatin, dibromomannitol, guanylhydrazone, ubenimex, octreotide acetate, tretinoin, porfimer sodium and the like), MMP inhibitor (marimastat, prinomastat and the like), angiogenesis inhibitor (neovastat, thalidomide, leflunomide, acetyldinalin, vitaxin and the like) and the like. Preferred are platinum complex compound (cisplatin, carboplatin, nedaplatin and the like), etoposide, paclitaxel, taxotere and the like, more preferred are cisplatin, etoposide and paclitaxel, and still more preferred is cisplatin.

The "antitumor effect" in the present invention intends to mean the action of the above-mentioned antitumor agent to act on tumor, particularly malignant tumor, and aid clinical remission of the cancer disease. For example, any action that brings about suppression of the growth of tumor cells, suppression of the infiltration metastasis of tumor cells, extension of the term before recurrence, extension of survival time of patients having a cancer, improvement of QOL of patients having a cancer, and the like.

In addition, the "treatment of tumor" in the present invention intends to mean action on tumor, particularly malignant tumor, to aid clinical remission of the cancer disease. It means, for example, any management (prophylaxis, treatment and the like of aggravation) in the treatment of tumor, particularly malignant tumor, such as suppression of the growth of tumor cells, suppression of the infiltration metastasis of tumor cells, extension of the term before recurrence, extension of survival time of patients having a cancer, improvement of QOL of patients having a cancer, and the like.

In the present invention, the "antitumor effect potentiator" comprises a compound having a Rho kinase inhibitory activity as an active ingredient and potentiates the antitumor effect of the antitumor agent by a combined use with the above-mentioned antitumor agent. Moreover, the "antitumor effect reinforcing action" means action to potentiate the antitumor effect of the above-mentioned antitumor agent.

The compound having a Rho kinase inhibitory activity, which is used as an active ingredient in the present invention, may be any as long as it has a Rho kinase inhibitory activity. In the present invention, Rho kinase means serine/threonine kinase activated along with the activation of Rho. For example, $ROK_\alpha$ (ROCKII: Leung, T. et al, J. Biol. Chem., 270, 29051–29054, 1995), p160 ROCK ($ROK_\beta$, ROCK-I: Ishizaki, T. et al, The EMBO J., 15(8), pp.1885–1893, 1996) and other proteins having a serine/threonine kinase activity are exemplified.

Examples of the compound having a Rho kinase inhibitory activity, which is used in the present invention, include the amide compound, isoquinolinesulfonamide derivative and isoquinoline derivative described in the above-mentioned WO98/06433, WO97/28130 and Naunyn-Schmiedeberg's Archives of Pharmacology 385(1), Suppl., R219 (1998), and vinyl benzene derivative and cinnamic acid derivative described in WO00/57914 and JP-A-2000-44513.

As the aforementioned amide compound, for example, a compound of the above-mentioned formula (I), particularly a compound of the formula (I'), are used. As the aforementioned isoquinolinesulfonamide derivative, hexahydro-1-(5-isoquinolinesulfonyl)-1H-1,4-diazepine hydrochloride [fasudil hydrochloride] and the like are used. As the aforementioned isoquinoline derivative, hexahydro-1-[(4-methyl-5-isoquinolinyl)sulfonyl]-1H-1,4-diazepine dihydrochloride, (S)-(+)-hexahydro-2-methyl-1-[(4-methyl-5-isoquinolinyl)sulfonyl]-1H-1,4-diazepine hydrochloride, hexahydro-7-methyl-1-[(4-methyl-5-isoquinolinyl) sulfonyl]-1H-1,4-diazepine dihydrochloride, hexahydro-5-methyl-1-[(4-methyl-5-isoquinolinyl)sulfonyl]-1H-1,4-diazepine dihydrochloride, hexahydro-2-methyl-1-[(4-methyl-5-isoquinolinyl)sulfonyl]-1H-1,4-diazepine hydrochloride, (R)-(−)-hexahydro-2-methyl-1-[(4-methyl-5-isoquinolinyl)-sulfonyl]-1H-1,4-diazepine hydrochloride, (R)-(+)-hexahydro-5-methyl-1-[(4-methyl-5-isoquinolinyl) sulfonyl]-1H-1,4-diazepine hydrochloride and the like are used.

As the aforementioned vinyl benzene derivative and cinnamic acid derivative, ethacrynic acid, 4-[2-(2,3,4,5,6-pentafluorophenyl)acryloyl]cinnamic acid and the like are mentioned.

It is preferably an amide compound represented by the formula (I), particularly preferably an amide compound represented by the formula (I').

In the present invention, one kind of a compound having a Rho kinase inhibitory activity may be used alone, or, where necessary, several kinds may be concurrently used.

In the present specification, each symbol of the formulas (I) and (I') is defined as follows.

Alkyl at R, R' and $R^1$ is linear or branched alkyl having 1 to 10 carbon atoms, which is exemplified by methyl, ethyl, propyl, isopropyl, butyl, isobutyl, sec-butyl, tert-butyl, pentyl, hexyl, heptyl, octyl, nonyl, decyl and the like, with preference given to alkyl having 1 to 4 carbon atoms.

Cycloalkyl at R, R' and $R^1$ has 3 to 7 carbon atoms and is exemplified by cyclopropyl, cyclobutyl, cyclopentyl, cyclohexyl, cycloheptyl and the like.

Cycloalkylalkyl at R, R' and $R^1$ is that wherein the cycloalkyl moiety is the above-mentioned cycloalkyl having 3 to 7 carbon atoms and the alkyl moiety is linear or branched alkyl having 1 to 6 carbon atoms (e.g., methyl, ethyl, propyl, isopropyl, butyl, pentyl, hexyl and the like), which is exemplified by cyclopropylmethyl, cyclobutylmethyl, cyclopentylmethyl, cyclohexylmethyl, cycloheptylmethyl, cyclopropylethyl, cyclobutylethyl, cyclopentylethyl, cyclohexylethyl, cycloheptylethyl, cyclopropylpropyl, cyclobutylpropyl, cyclopentylpropyl, cyclohexylpropyl, cycloheptylpropyl, cyclopropylbutyl, cyclobutylbutyl, cyclopentylbutyl, cyclohexylbutyl, cycloheptylbutyl, cyclopropylhexyl, cyclobutylhexyl, cyclopentylhexyl, cyclohexylhexyl, cycloheptylhexyl and the like.

Aralkyl at R, R' and $R^1$ is that wherein alkyl moiety is alkyl having 1 to 4 carbon atoms and is exemplified by phenylalkyl such as benzyl, 1-phenylethyl, 2-phenylethyl, 3-phenylpropyl, 4-phenylbutyl and the like.

The substituent of optionally substituted cycloalkyl, cycloalkylalkyl, phenyl and aralkyl on the ring at R, R' and $R^1$ is halogen (e.g., chlorine, bromine, fluorine and iodine), alkyl (same as alkyl at R, R' and $R^1$), alkoxy (linear or branched alkoxy having 1 to 6 carbon atoms, such as methoxy, ethoxy, propoxy, isopropoxy, butoxy, isobutoxy, sec-butoxy, tert-butoxy, pentyloxy, hexyloxy and the like), aralkyl (same as aralkyl at R, R' and $R^1$) or haloalkyl (alkyl at R, R' and $R^1$ which is substituted by 1–5 halogen, and exemplified by fluoromethyl, difluoromethyl, trifluoromethyl, 2,2,2-trifluoroethyl, 2,2,3,3,3-pentafluoropropyl and the like), nitro, amino, cyano, azide and the like.

The group formed by R and $R^1$ or R' and $R^1$ in combination together with the adjacent nitrogen atom, which forms a heterocycle optionally further having, in the ring, oxygen atom, sulfur atom or optionally substituted nitrogen atom is preferably a 5 or 6-membered ring and bonded ring thereof. Examples thereof include 1-pyrrolidinyl, piperidino, 1-piperazinyl, morpholino, thiomorpholino, 1-imidazolyl, 2,3-dihydrothiazol-3-yl and the like. The substituent of the optionally substituted nitrogen atom is exemplified by alkyl, aralkyl, haloalkyl and the like. As used herein, alkyl, aralkyl and haloalkyl are as defined for R, R' and $R^1$.

Alkyl at $R^2$ is as defined for R, R' and $R^1$.

Halogen, alkyl, alkoxy and aralkyl at $R^3$ and $R^4$ are as defined for R, R' and $R^1$.

Acyl at $R^3$ and $R^4$ is alkanoyl having 2 to 6 carbon atoms (e.g., acetyl, propionyl, butyryl, valeryl, pivaloyl and the like), benzoyl or phenylalkanoyl wherein the alkanoyl moiety has 2 to 4 carbon atoms (e.g., phenylacetyl, phenylpropionyl, phenylbutyryl and the like).

Alkylamino at $R^3$ and $R^4$ is that wherein the alkyl moiety is linear or branched alkyl having 1 to 6 carbon atoms. Examples thereof include methylamino, ethylamino, propylamino, isopropylamino, butylamino, isobutylamino, sec-butylamino, tert-butylamino, pentylamino, hexylamino and the like.

Acylamino at $R^3$ and $R^4$ is that wherein acyl moiety is alkanoyl having 2 to 6 carbon atoms, benzoyl or the alkanoyl moiety is phenylalkanoyl having 2 to 4 carbon atoms and the like, which is exemplified by acetylamino, propionylamino, butyrylamino, valerylamino, pivaloylamino, benzoylamino, phenylacetylamino, phenylpropionylamino, phenylbutyrylamino and the like.

Alkylthio at $R^3$ and $R^4$ is that wherein the alkyl moiety is linear or branched alkyl having 1 to 6 carbon atoms, which is exemplified by methylthio, ethylthio, propylthio, isopropylthio, butylthio, isobutylthio, sec-butylthio, tert-butylthio, pentylthio, hexylthio and the like.

Aralkyloxy at $R^3$ and $R^4$ is that wherein the alkyl moiety is alkyl having 1 to 4 carbon atoms, which is exemplified by benzyloxy, 1-phenylethyloxy, 2-phenylethyloxy, 3-phenylpropyloxy, 4-phenylbutyloxy and the like.

Aralkylthio at $R^3$ and $R^4$ is that wherein the alkyl moiety is alkyl having 1 to 4 carbon atoms, which is exemplified by benzylthio, 1-phenylethylthio, 2-phenylethylthio, 3-phenylpropylthio, 4-phenylbutylthio and the like.

Alkoxycarbonyl at $R^3$ and $R^4$ is that wherein the alkoxy moiety is linear or branched alkoxy having 1 to 6 carbon atoms, which is exemplified by methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl and the like.

Mono- or di-alkylcarbamoyl at $R^3$ and $R^4$ is carbamoyl mono- or di-substituted by alkyl having 1 to 4 carbon atoms, which is exemplified by methylcarbamoyl, dimethylcarbamoyl, ethylcarbamoyl, diethylcarbamoyl, propylcarbamoyl, dipropylcarbamoyl, butylcarbamoyl, dibutylcarbamoyl and the like.

Alkoxy at $R^5$ is as defined for R, R' and $R^1$.

Alkoxycarbonyloxy at $R^5$ is that wherein the alkoxy moiety is linear or branched alkoxy having 1 to 6 carbon atoms, which is exemplified by methoxycarbonyloxy, ethoxycarbonyloxy, propoxycarbonyloxy, isopropoxycarbonyloxy, butoxycarbonyloxy, isobutoxycarbonyloxy, sec-butoxycarbonyloxy, tert-butoxycarbonyloxy, pentyloxycarbonyloxy, hexyloxycarbonyloxy and the like.

Alkanoyloxy at $R^5$ is that wherein the alkanoyl moiety is alkanoyl having 2 to 6 carbon atoms, which is exemplified by acetyloxy, propionyloxy, butyryloxy, valeryloxy, pivaloyloxy and the like.

Aralkyloxycarbonyloxy at $R^5$ is that wherein the aralkyl moiety is aralkyl having $C_1$–$C_4$ alkyl, which is exemplified by benzyloxycarbonyloxy, 1-phenylethyloxycarbonyloxy, 2-phenylethyloxycarbonyloxy, 3-phenylpropyloxycarbonyloxy, 4-phenylbutyloxycarbonyloxy and the like.

Alkyl at $R^6$ is as defined for R, R' and $R^1$; alkyl at $R^8$ and $R^9$ is as defined for R, R' and $R^1$; and aralkyl at $R^8$ and $R^9$ is as defined for R, R' and $R^1$.

Alkyl at $R^7$ is as defined for R, R' and $R^1$ and aralkyl at $R^7$ is as defined for R, R' and $R^1$.

The group formed by $R^6$ and $R^7$ in combination, which forms a heterocycle optionally further having, in the ring, oxygen atom, sulfur atom or optionally substituted nitrogen atom, is exemplified by imidazol-2-yl, thiazol-2-yl, oxazol-2-yl, imidazolin-2-yl, 3,4,5,6-tetrahydropyridin-2-yl, 3,4,5,6-tetrahydropyrimidin-2-yl, 1,3-oxazolin-2-yl, 1,3-thiazolin-2-yl, or benzoimidazol-2-yl, benzothiazol-2-yl, benzoxazol-2-yl and the like optionally having a substituent such as halogen, alkyl, alkoxy, haloalkyl, nitro, amino, phenyl, aralkyl and the like. As used herein, halogen, alkyl, alkoxy, haloalkyl and aralkyl are as defined for R, R' and $R^1$.

The substituent of the above-mentioned optionally substituted nitrogen atom is exemplified by alkyl, aralkyl, haloalkyl and the like. As used herein, alkyl, aralkyl and haloalkyl are as defined for R, R' and $R^1$.

Hydroxyalkyl at $R^{10}$ and $R^{11}$ is linear or branched alkyl having 1 to 6 carbon atoms which is substituted by 1 to 3 hydroxy, which is exemplified by hydroxymethyl, 2-hydroxyethyl, 1-hydroxyethyl, 3-hydroxypropyl, 4-hydroxybutyl and the like.

Alkyl at $R^{10}$ and $R^{11}$ is as defined for R, R' and $R^1$; haloalkyl and alkoxycarbonyl at $R^{10}$ and $R^{11}$ are as defined for R, R' and $R^1$; aralkyl at $R^{10}$ and $R^{11}$ is as defined for R, R' and $R^1$.

Cycloalkyl formed by $R^{10}$ and $R^{11}$ in combination is the same as cycloalkyl at R, R' and $R^1$.

Alkyl at L is as defined for R, R' and $R^1$.

Aminoalky at L is a linear or branched alkyl having 1 to 6 carbon atoms, which is substituted by amino, which is exemplified by aminomethyl, 2-aminoethyl, 1-aminoethyl, 3-aminopropyl, 4-aminobutyl, 5-aminopentyl, 6-aminohexyl and the like.

Mono- or dialkylaminoalkyl at L is mono- or di-substituted aminoalkyl with alkyl having 1 to 4 carbon atoms, which is exemplified by methylaminomethyl, dimethylaminomethyl, ethylaminomethyl, diethylaminomethyl, propylaminomethyl, dipropylaminomethyl, butylaminomethyl, dibutylaminomethyl, 2-dimethylaminoethyl, 2-diethylaminoethyl and the like.

Carbamoylalkyl at L is linear or branched alkyl having 1 to 6 carbon atoms substituted by carbamoyl, which is exemplified by carbamoylmethyl, 2-carbamoylethyl, 1-carbamoylethyl, 3-carbamoylpropyl, 4-carbamoylbutyl, 5-carbamoylpentyl, 6-carbamoylhexyl and the like.

Phthalimidoalkyl at L is linear or branched alkyl having 1 to 6 carbon atoms, which is substituted by phthalimide. Examples thereof include phthalimidomethyl, 2-phthalimidoethyl, 1-phthalimidoethyl, 3-phthalimidopropyl, 4-phthalimidobutyl, 5-phthalimidopentyl, 6-phthalimidohexyl and the like.

Alkyl at B is as defined for R, R' and $R^1$.

Alkoxy at B is as defined for R, R' and $R^1$.

Aralkyl at B is as defined for R, R' and $R^1$.

Aralkyloxy at B is as defined for $R^3$ and $R^4$.

Aminoalkyl at B is as defined for L.

Hydroxyalkyl at B is as defined for $R^{10}$ and $R^{11}$.

Alkanoyloxyalkyl at B is that wherein linear or branched alkyl having 1 to 6 carbon atoms is substituted by alkanoyloxy having alkanoyl moiety having 2 to 6 carbon atoms, which is exemplified by acetyloxymethyl, propionyloxymethyl, butyryloxymethyl, valeryloxymethyl, pivaloyloxymethyl, acetyloxyethyl, propionyloxyethyl, butyryloxyethyl, valeryloxyethyl, pivaloyloxyethyl and the like.

Alkoxycarbonylalkyl at B is that wherein linear or branched alkyl having 1 to 6 carbon atoms is substituted by alkoxycarbonyl having alkoxy moiety having 1 to 6 carbon atoms, which is exemplified by methoxycarbonylmethyl, ethoxycarbonylmethyl, propoxycarbonylmethyl, isopropoxycarbonylmethyl, butoxycarbonylmethyl, isobutoxycarbonylmethyl, sec-butoxycarbonylmethyl, tert-butoxycarbonylmethyl, pentyloxycarbonylmethyl, hexyloxycarbonylmethyl, methoxycarbonylethyl, ethoxycarbonylethyl, propoxycarbonylethyl, isopropoxycarbonylethyl, butoxycarbonylethyl, isobutoxycarbonylethyl, sec-butoxycarbonylethyl, tert-butoxycarbonylethyl, pentyloxycarbonylethyl, hexyloxycarbonylethyl and the like.

Halogen at $Q^1$, $Q^2$ and $Q^3$ is as defined for R, R' and $R^1$.

Aralkyloxy at $Q^1$ and $Q^2$ is as defined for $R^3$ and $R^4$.

Alkoxy at $Q^3$ is as defined for R, R' and $R^1$.

Alkylene at W, X and Y is linear or branched alkylene having 1 to 6 carbon atoms, which is exemplified by methylene, ethylene, trimethylene, propylene, tetramethylene, pentamethylene, hexamethylene and the like.

Alkenylene at Y is linear or branched alkenylene having 2 to 6 carbon atoms, which is exemplified by vinylene, propenylene, butenylene, pentenylene and the like.

Alkyl at Rb is as defined for R, R' and $R^1$.

Aralkyl at Rb is as defined for R, R' and $R^1$.

Aminoalkyl at Rb is as defined for L.

Mono- or dialkylaminoalkyl at Rb is as defined for L.

The nitrogen-containing heterocycle at Rc, when it is a monocyclic ring, is exemplified by pyridine, pyrimidine, pyridazine, triazine, pyrazole, triazole and the like, and when it is a condensed ring, it is exemplified by pyrrolopyridine (e.g., 1H-pyrrolo[2,3-b]pyridine, 1H-pyrrolo[3,2-b]pyridine, 1H-pyrrolo[3,4-b]pyridine and the like), pyrazolopyridine (e.g., 1H-pyrazolo[3,4-b]pyridine, 1H-pyrazolo[4,3-b]pyridine and the like), imidazopyridine (e.g., 1H-imidazo[4,5-b]pyridine and the like), pyrrolopyrimidine (e.g., 1H-pyrrolo[2,3-d]pyrimidine, 1H-pyrrolo[3,2-d]pyrimidine, 1H-pyrrolo[3,4-d]pyrimidine and the like), pyrazolopyrimidine (e.g., 1H-pyrazolo[3,4-d]pyrimidine, pyrazolo[1,5-a]pyrimidine, 1H-pyrazolo[4,3-d]pyrimidine and the like), imidazopyrimidine (e.g., imidazo[1,2-a]pyrimidine, 1H-imidazo[4,5-d]pyrimidine and the like), pyrrolotriazine (e.g., pyrrolo[1,2-a]-1,3,5-triazine, pyrrolo[2,1-f]-1,2,4-triazine), pyrazolotriazine (e.g., pyrazolo[1,5-a]-1,3,5-triazine and the like), triazolopyridine (e.g., 1H-1,2,3-triazolo[4,5-b]pyridine and the like), triazolopyrimidine (e.g., 1,2,4-triazolo[1,5-a]pyrimidine, 1,2,4-triazolo[4,3-a]pyrimidine, 1H-1,2,3-triazolo[4,5-d]pyrimidine and the like), cinnoline, quinazoline, quinoline, pyridopyridazine (e.g., pyrido[2,3-c]pyridazine and the like), pyridopyrazine (e.g., pyrido[2,3-b]pyrazine and the like), pyridopyrimidine (e.g., pyrido[2,3-d]pyrimidine, pyrido[3,2-d]pyrimidine and the like), pyrimidopyrimidine (e.g., pyrimido[4,5-d]pyrimidine, pyrimido[5,4-d]pyrimidine and the like), pyrazinopyrimidine (e.g., pyrazino[2,3-d]pyrimidine and the like), naphthyridine (e.g., 1,8-naphthyridine and the like), tetrazolopyrimidine (e.g., tetrazolo[1,5-a]pyrimidine and the like), thienopyridine (e.g., thieno[2,3-b]pyridine and the like), thienopyrimidine (e.g., thieno[2,3-d]pyrimidine and the like), thiazolopyridine (e.g., thiazolo[4,5-b]pyridine, thiazolo[5,4-b]pyridine and the like), thiazolopyrimidine (e.g., thiazolo[4,5-d]pyrimidine, thiazolo[5,4-d]pyrimidine and the like), oxazolopyridine (e.g., oxazolo[4,5-b]pyridine, oxazolo[5,4-b]pyridine and the like), oxazolopyrimidine (e.g., oxazolo[4,5-d]pyrimidine, oxazolo[5,4-d]pyrimidine and the like), furopyridine (e.g., furo[2,3-b]pyridine, furo[3,2-b]pyridine and the like), furopyrimidine (e.g., furo[2,3-d]ypyrimidine, furo[3,2-d]pyrimidine and the like), 2,3-dihydropyrrolopyridine (e.g., 2,3-dihydro-1H-pyrrolo[2,3-b]pyridine, 2,3-dihydro-1H-pyrrolo[3,2-b]pyridine and the like), 2,3-dihydropyrrolopyrimidine (e.g., 2,3-dihydro-1H- pyrrolo[2,3-d]pyrimidine, 2,3-dihydro-1H-pyrrolo[3,2-d] pyrimidine and the like), 5,6,7,8-tetrahydropyrido[2,3-d] pyrimidine, 5,6,7,8-tetrahydro-1,8-naphthyridine, 5,6,7,8-tetrahydroquinoline and the like. When these rings form a hydrogenated aromatic ring, the carbon atom in the ring may be carbonyl and includes, for example, 2,3-dihydro-2-oxopyrrolopyridine, 2,3-dihydro-2,3-dioxopyrrolopyridine, 7,8-dihydro-7-oxo-1,8-naphthyridine, 5,6,7,8-tetrahydro-7-oxo-1,8-naphthyridine and the like.

These rings may be substituted by a substituent such as halogen, alkyl, alkoxy, aralkyl, haloalkyl, nitro, amino, alkylamino, cyano, formyl, acyl, aminoalkyl, mono- or dialkylaminoalkyl, azide, carboxy, alkoxycarbonyl, carbamoyl, mono- or di-alkylcarbamoyl, alkoxyalkyl (e.g., methoxymethyl, methoxyethyl, methoxypropyl, ethoxymethyl, ethoxyethyl, ethoxypropyl and the like), optionally substituted hydrazino and the like.

As used herein, the substituent of the optionally substituted hydrazino includes alkyl, aralkyl, nitro, cyano and the like, wherein alkyl and aralkyl are as defined for R, R' and $R^1$ and exemplified by methylhydrazino, ethylhydrazino, benzylhydrazino and the like.

The compound of the formula (I) is exemplified by the following compounds.
(1) 4-(2-pyridylcarbamoyl)piperidine
(2) 1-benzyloxycarbonyl-4-(4-pyridylcarbamoyl)piperidine
(3) 1-benzoyl-4-(4-pyridylcarbamoyl)piperidine
(4) 1-propyl-4-(4-pyridylcarbamoyl)piperidine
(5) 1-[3-(2-(2-thienylmethyl)phenoxy)-2-hydroxypropyl]-4-(4-pyridylcarbamoyl)piperidine
(6) 4-(4-pyridylcarbamoyl)piperidine
(7) 1-benzyl-4-(4-pyridylcarbamoyl)-1,2,5,6-tetrahydropyridine
(8) 3-(4-pyridylcarbamoyl)piperidine
(9) 1-benzyl-3-(4-pyridylcarbamoyl)piperidine
(10) 1-(2-(4-benzyloxyphenoxy)ethyl)-4-(N-(2-pyridyl)-N-benzylcarbamoyl)piperidine
(11) 1-formyl-4-(4-pyridylcarbamoyl)piperidine
(12) 4-(3-pyridylcarbamoyl)piperidine
(13) 1-isopropyl-4-(4-pyridylcarbamoyl)piperidine
(14) 1-methyl-4-(4-pyridylcarbamoyl)piperidine
(15) 1-hexyl-4-(4-pyridylcarbamoyl)piperidine
(16) 1-benzyl-4-(4-pyridylcarbamoyl)piperidine
(17) 1-(2-phenylethyl)-4-(4-pyridylcarbamoyl)piperidine
(18) 1-(2-(4-methoxyphenyl)ethyl)-4-(4-pyridylcarbamoyl)piperidine
(19) 1-(2-(4-methoxyphenyl)ethyl)-4-(2-pyridylcarbamoyl)piperidine
(20) 1-(2-(4-chlorophenyl)ethyl)-4-(4-pyridylcarbamoyl)piperidine
(21) 1-diphenylmethyl-4-(2-pyridylcarbamoyl)piperidine
(22) 1-[2-(4-(5-methyl-3-oxo-2,3,4,5-tetrahydropyridazin-6-yl)phenyl)ethyl]-4-(2-pyridylcarbamoyl)piperidine
(23) 1-(4-(4,5-dihydro-2-furyl)phenyl)-4-(4-pyridylcarbamoyl)piperidine
(24) 1-(2-nitrophenyl)-4-(4-pyridylcarbamoyl)piperidine
(25) 1-(2-aminophenyl)-4-(4-pyridylcarbamoyl)piperidine
(26) 1-nicotinoyl-4-(4-pyridylcarbamoyl)piperidine
(27) 1-isonicotinoyl-4-(4-pyridylcarbamoyl)piperidine
(28) 1-(3,4,5-trimethoxybenzoyl)-4-(4-pyridylcarbamoyl)piperidine
(29) 1-acetyl-4-(4-pyridylcarbamoyl)piperidine
(30) 1-(3-(4-fluorobenzoyl)propyl)-4-(4-pyridylcarbamoyl)piperidine
(31) 1-(3-(4-fluorobenzoyl)propyl)-4-(2-pyridylcarbamoyl)piperidine
(32) 1-(1-(4-hydroxybenzoyl)ethyl)-4-(2-pyridylcarbamoyl)piperidine
(33) 1-(1-(4-benzyloxybenzoyl)ethyl)-4-(2-pyridylcarbamoyl)piperidine
(34) 1-(2-(4-hydroxyphenoxy)ethyl)-4-(2-pyridylcarbamoyl)piperidine
(35) 1-(4-(4-fluorophenyl)-4-hydroxybutyl)-4-(4-pyridylcarbamoyl)piperidine
(36) 1-(1-methyl-2-(4-hydroxyphenyl)-2-hydroxyethyl)-4-(2-pyridylcarbamoyl)piperidine
(37) 1-cinnamyl-4-(2-pyridylcarbamoyl)piperidine
(38) 1-(2-hydroxy-3-phenoxypropyl)-4-(4-pyridylcarbamoyl)piperidine
(39) 1-(2-hydroxy-3-phenoxypropyl)-4-(3-pyridylcarbamoyl)piperidine
(40) 1-(2-hydroxy-3-phenoxypropyl)-4-(2-pyridylcarbamoyl)piperidine
(41) 1-(2-phenylethyl)-4-[N-(2-pyridyl)-N-(2-(N,N-dimethylamino)ethyl)carbamoyl]piperidine
(42) 1-benzyloxycarbonyl-4-(2-pyridylcarbamoyl)piperidine
(43) 1-(3-chlorophenyl)carbamoyl-4-(4-pyridylcarbamoyl)piperidine
(44) 4-[N-(2-pyridyl)-N-(2-(N,N-dimethylamino)ethyl)-carbamoyl]piperidine
(45) 1-methyl-4-(4-pyridylcarbamoyl)-1,2,5,6-tetrahydropyridine
(46) 1-nicotinoyl-3-(4-pyridylcarbamoyl)piperidine
(47) 1-[2-(4-fluorobenzoyl)ethyl]-4-(4-pyridylcarbamoyl)piperidine
(48) 1-(6-chloro-2-methylimidazo[1,2-a]pyridine-3-carbonyl)-4-(4-pyridylcarbamoyl)piperidine
(49) 1-(4-nitrobenzyl)-4-(4-pyridylcarbamoyl)piperidine
(50) 1-hexyl-4-(4-pyridylcarbamoyl)piperidine
(51) 1-benzyloxycarbonyl-4-(2-chloro-4-pyridylcarbamoyl)piperidine
(52) 4-(2-chloro-4-pyridylcarbamoyl)piperidine
(53) 1-(2-chloronicotinoyl)-4-(4-pyridylcarbamoyl)piperidine
(54) 3-(2-chloro-4-pyridylcarbamoyl)piperidine
(55) 1-(4-phthalimidobutyl)-4-(4-pyridylcarbamoyl)piperidine
(56) 1-(3,5-di-tert-butyl-4-hydroxycinnamoyl)-4-(4-pyridylcarbamoyl)piperidine
(57) 1-carbamoylmethyl-4-(4-pyridylcarbamoyl)piperidine
(58) 1-benzyloxycarbonyl-4-(5-nitro-2-pyridylcarbamoyl)piperidine
(59) 4-(5-nitro-2-pyridylcarbamoyl)piperidine
(60) trans-4-benzyloxycarboxamidomethyl-1-(4-pyridylcarbamoyl)cyclohexane
(61) trans-4-aminomethyl-1-(4-pyridylcarbamoyl)cyclohexane
(62) trans-4-formamidomethyl-1-(4-pyridylcarbamoyl)cyclohexane
(63) trans-4-dimethylaminomethyl-1-(4-pyridylcarbamoyl)cyclohexane
(64) N-benzylidene-trans-(4-pyridylcarbamoyl)cyclohexylmethylamine
(65) trans-4-benzylaminomethyl-1-(4-pyridylcarbamoyl)cyclohexane
(66) trans-4-isopropylaminomethyl-1-(4-pyridylcarbamoyl)cyclohexane
(67) trans-4-nicotinoylaminomethyl-1-(4-pyridylcarbamoyl)cyclohexane
(68) trans-4-cyclohexylaminomethyl-1-(4-pyridylcarbamoyl)cyclohexane
(69) trans-4-benzyloxycarboxamide-1-(4-pyridylcarbamoyl)cyclohexane
(70) trans-4-amino-1-(4-pyridylcarbamoyl)cyclohexane

(71) trans-4-(1-aminoethyl)-1-(4-pyridylcarbamoyl)cyclohexane
(72) trans-4-aminomethyl-cis-2-methyl-1-(4-pyridylcarbamoyl)cyclohexane
(73) (+)-trans-4-(1-benzyloxycarboxamidopropyl)-1-cyclohexanecarboxylic acid
(74) (+)-trans-4-(l-benzyloxycarboxamidopropyl)-1-(4-pyridylcarbamoyl)cyclohexane
(75) (−)-trans-4-(1-benzyloxycarboxamidopropyl)-1-(4-pyridylcarbamoyl)cyclohexane
(76) (+)-trans-4-(1-aminopropyl)-1-(4-pyridylcarbamoyl)cyclohexane
(77) (−)-trans-4-(1-aminopropyl)-1-(4-pyridylcarbamoyl)cyclohexane
(78) (−)-trans-4-(1-benzyloxycarboxamidoethyl)-1-(4-pyridylcarbamoyl)cyclohexane
(79) (+)-trans-4-(1-benzyloxycarboxamidoethyl)-1-(4-pyridylcarbamoyl)cyclohexane
(80) (+)-trans-4-(1-aminoethyl)-1-(4-pyridylcarbamoyl)cyclohexane
(81) (−)-trans-4-(1-aminoethyl)-1-(4-pyridylcarbamoyl)cyclohexane
(82) trans-4-(4-chlorobenzoyl)aminomethyl-1-(4-pyridylcarbamoyl)cyclohexane
(83) trans-4-aminomethyl-1-(2-pyridylcarbamoyl)cyclohexane
(84) trans-4-benzyloxycarboxamidomethyl-1-(2-pyridylcarbamoyl)cyclohexane
(85) trans-4-methylaminomethyl-1-(4-pyridylcarbamoyl)cyclohexane
(86) trans-4-(N-benzyl-N-methylamino)methyl-1-(4-pyridylcarbamoyl)cyclohexane
(87) trans-4-aminomethyl-1-(3-pyridylcarbamoyl)cyclohexane
(88) trans-4-aminomethyl-1-[(3-hydroxy-2-pyridyl)carbamoyl]cyclohexane
(89) trans-4-benzyloxycarboxamidomethyl-1-(3-pyridylcarbamoyl)cyclohexane
(90) trans-4-benzyloxycarboxamidomethyl-1-[(3-benzyloxy-2-pyridyl)carbamoyl]cyclohexane
(91) trans-4-phthalimidomethyl-1-(4-pyridylcarbamoyl)cyclohexane
(92) trans-4-benzyloxycarboxamidomethyl-1-(3-methyl-4-pyridylcarbamoyl)cyclohexane
(93) trans-4-aminomethyl-1-(3-methyl-4-pyridylcarbamoyl)cyclohexane
(94) 4-(trans-4-benzyloxycarboxamidomethylcyclohexylcarbonyl)amino-2,6-dimethylpyridine-N-oxide
(95) 4-(trans-4-aminomethylcyclohexylcarbonyl)amino-2,6-dimethylpyridine-N-oxide
(96) trans-4-aminomethyl-1-(2-methyl-4-pyridylcarbamoyl)cyclohexane
(97) trans-4-(1-benzyloxycarboxamidoethyl)-1-(4-pyridylcarbamoyl)cyclohexane
(98) trans-4-(1-amino-1-methylethyl)-1-(4-pyridylcarbamoyl)cyclohexane
(99) trans-4-(2-aminoethyl)-1-(4-pyridylcarbamoyl)cyclohexane
(100) trans-4-(2-amino-1-methylethyl)-1-(4-pyridylcarbamoyl)cyclohexane
(101) trans-4-(1-aminopropyl)-1-(4-pyridylcarbamoyl)cyclohexane
(102) trans-4-aminomethyl-trans-1-methyl-1-(4-pyridylcarbamoyl)cyclohexane
(103) trans-4-benzylaminomethyl-cis-2-methyl-1-(4-pyridylcarbamoyl)cyclohexane
(104) trans-4-(1-benzyloxycarboxamide-1-methylethyl)-1-(4-pyridylcarbamoyl)cyclohexane
(105) trans-4-benzyloxycarboxamidomethyl-1-(N-methyl-4-pyridylcarbamoyl)cyclohexane
(106) trans-4-(1-acetamide-1-methylethyl)-1-(4-pyridylcarbamoyl)cyclohexane
(107) trans-N-(6-amino-4-pyrimidyl)-4-aminomethylcyclohexanecarboxamide
(108) trans-N-(1H-pyrrolo[2,3-b]pyridin-4-yl)-4-aminomethylcyclohexanecarboxamide
(109) (+)-trans-N-(1H-pyrrolo[2,3-b]pyridin-4-yl)-4-(1-aminoethyl)cyclohexanecarboxamide
(110) trans-N-(1H-pyrrolo[2,3-b]pyridin-4-yl)-4-(1-amino-1-methylethyl)cyclohexanecarboxamide
(111) trans-N-(1H-pyrazolo[3,4-b]pyridin-4-yl)-4-aminomethylcyclohexanecarboxamide
(112) (+)-trans-N-(1H-pyrazolo[3,4-b]pyridin-4-yl)-4-(1-aminoethyl)cyclohexanecarboxamide
(113) trans-N-(1H-pyrazolo[3,4-b]pyridin-4-yl)-4-(1-amino-1-methylethyl)cyclohexanecarboxamide
(114) (+)-trans-N-(2-amino-4-pyridyl)-4-(1-aminoethyl)cyclohexanecarboxamide
(115) trans-N-(1H-pyrazolo[3,4-d]pyrimidin-4-yl)-4-aminomethylcyclohexanecarboxamide
(116) (+)-trans-N-(1H-pyrazolo[3,4-d]pyrimidin-4-yl)-4-(1-aminoethyl)cyclohexanecarboxamide
(117) trans-N-(1H-pyrazolo[3,4-d]pyrimidin-4-yl)-4-(1-amino-1-methylethyl)cyclohexanecarboxamide
(118) trans-N-(4-pyrimidinyl)-4-aminomethylcyclohexanecarboxamide
(119) trans-N-(3-amino-4-pyridyl)-4-aminomethylcyclohexanecarboxamide
(120) trans-N-(7H-imidazo[4,5-d]pyrimidin-6-yl)-4-aminomethylcyclohexanecarboxamide
(121) trans-N-(3H-1,2,3-triazolo[4,5-d]pyrimidin-7-yl)-4-aminomethylcyclohexanecarboxamide
(122) trans-N-(1-benzyl-1H-pyrazolo[3,4-b]pyridin-4-yl)-4-aminomethylcyclohexanecarboxamide
(123) trans-N-(1H-5-pyrazolyl)-4-aminomethylcyclohexanecarboxamide
(124) trans-N-(1H-pyrazolo[3,4-b]pyridin-4-yl)-4-aminomethylcyclohexanecarboxamide
(125) trans-N-(4-pyridazinyl)-4-aminomethylcyclohexanecarboxamide
(126) trans-N-(7H-pyrrolo[2,3-d]pyrimidin-4-yl)-4-aminomethylcyclohexanecarboxamide
(127) trans-N-(2-amino-4-pyridyl)-4-aminomethylcyclohexanecarboxamide
(128) trans-N-(thieno[2,3-d]pyrimidin-4-yl)-4-aminomethylcyclohexanecarboxamide
(129) trans-N-(5-methyl-1,2,4-triazolo[1,5-a]pyrimidin-7-yl)-4-aminomethylcyclohexanecarboxamide
(130) trans-N-(3-cyano-5-methylpyrazolo[1,5-a]pyrimidin-7-yl)-4-aminomethylcyclohexanecarboxamide
(131) trans-N-(1H-pyrazolo[3,4-b]pyridin-4-yl)-4-(l-amino-1-methylethyl)cyclohexanecarboxamide
(132) trans-N-(2-(1-pyrrolidinyl)-4-pyridyl)-4-aminomethylcyclohexanecarboxamide
(133) trans-N-(2,6-diamino-4-pyrimidyl)-4-aminomethylcyclohexanecarboxamide
(134) (+)-trans-N-(7-methyl-1,8-naphthyridin-4-yl)-4-(1-aminoethyl)cyclohexanecarboxamide
(135) trans-N-(1-benzyloxymethylpyrrolo[2,3-b]pyridin-4-yl)-4-aminomethylcyclohexanecarboxamide
(136) (+)-trans-N-(1-methylpyrrolo[2,3-b]pyridin-4-yl)-4-(1-aminoethyl)cyclohexanecarboxamide
(137) trans-N-benzyl-N-(2-benzylamino-4-pyridyl)-4-(1-amino-1-methylethyl)cyclohexanecarboxamide
(138) trans-N-(2-azide-4-pyridyl)-4-aminomethylcyclohexanecarboxamide (139) trans-N-(2,3-dihydro-1H-pyrrolo[2,3-b]pyridin-4-yl)-4-aminomethylcyclohexanecarboxamide
(140) trans-N-(2,3-dihydro-1H-pyrrolo[2,3-b]pyridin-4-yl)-4-(1-amino-1-methylethyl)cyclohexanecarboxamide
(141-1) trans-N-(2-carboxy-4-pyridyl)-4-aminomethylcyclohexanecarboxamide
(141-2) (R)-(+)-trans-N-(3-bromo-1H-pyrrolo[2,3-b]pyridin-4-yl)-4-(1-aminoethyl)cyclohexanecarboxamide
(142) trans-N-(1H-pyrrolo[2,3-b]pyridin-4-yl)-4-guanidinomethylcyclohexanecarboxamide
(143) trans-N-(1H-pyrazolo[3,4-b]pyridin-4-yl)-4-guanidinomethylcyclohexanecarboxamide
(144) trans-N-(4-pyridyl)-4-guanidinomethylcyclohexanecarboxamide
(145) trans-N-(1-methylpyrrolo[2,3-b]pyridin-4-yl)-4-(guanidinomethyl)cyclohexanecarboxamide
(146) trans-N-(1H-pyrrolo[2,3-b]pyridin-4-yl)-4-(2-imidazolin-2-yl)aminomethylcyclohexanecarboxamide
(147) trans-N-(1-benzyloxymethylpyrrolo[2,3-b]pyridin-4-yl)-4-guanidinomethylcyclohexanecarboxamide
(148) trans-N-(2-amino-4-pyridyl)-4-guanidinomethylcyclohexanecarboxamide
(149) trans-N-(1-benzyloxymethyl-1H-pyrrolo[2,3-b]pyridin-4-yl)-4-(2-imidazolin-2-yl)aminomethylcyclohexanecarboxamide
(150) trans-N-(1H-pyrrolo[2,3-b]pyridin-4-yl)-4-(3-benzylguanidinomethyl)cyclohexanecarboxamide
(151) trans-N-(1H-pyrrolo[2,3-b]pyridin-4-yl)-4-(3-phenylguanidinomethyl)cyclohexanecarboxamide
(152) trans-N-(1H-pyrrolo[2,3-b]pyridin-4-yl)-4-(3-propylguanidinomethyl)cyclohexanecarboxamide
(153) trans-N-(1H-pyrrolo[2,3-b]pyridin-4-yl)-4-(3-octylguanidinomethyl)cyclohexanecarboxamide
(154) trans-N-(1-benzyloxymethylpyrrolo[2,3-b]pyridin-4-yl)-4-(2-benzyl-3-ethylguanidinomethyl)cyclohexanecarboxamide
(155) trans-N-(1H-pyrrolo[2,3-b]pyridin-4-yl)-4-(imidazol-2-yl)aminomethylcyclohexanecarboxamide
(156) trans-N-(1H-pyrrolo[2,3-b]pyridin-4-yl)-4-(thiazol-2-yl)aminomethylcyclohexanecarboxamide
(157) (R)-(+)-N-(4-pyridyl)-4-(1-aminoethyl)benzamide
(158) N-(4-pyridyl)-4-(1-amino-1-methylethyl)benzamide
(159) N-(4-pyridyl)-4-aminomethyl-2-benzyloxybenzamide
(160) N-(4-pyridyl)-4-aminomethyl-2-ethoxybenzamide
(161) (R)-(−)-N-(4-pyridyl)-4-(1-aminoethyl)-3-nitrobenzamide
(162) (R)-(−)-N-(4-pyridyl)-3-amino-4-(1-aminoethyl)benzamide
(163) (R)-(+)-N-(4-pyridyl)-4-(1-aminoethyl)-3-chlorobenzamide
(164) N-(4-pyridyl)-3-aminomethylbenzamide
(165) (R)-(+)-N-(1H-pyrrolo[2,3-b]pyridin-4-yl)-4-(1-aminoethyl)benzamide
(166) (R)-(+)-N-(1H-pyrazolo[3,4-b]pyridin-4-yl)-4-(1-aminoethyl)benzamide
(167) N-(1H-pyrazolo[3,4-b]pyridin-4-yl)-4-guanidinomethylbenzamide
(168) N-(4-pyridyl)-4-guanidinomethylbenzamide
(169) (R)-(+)-N-(4-pyridyl)-4-(1-aminoethyl)-3-fluorobenzamide
(170) N-(4-pyridyl)-4-aminomethylbenzamide
(171) N-(4-pyridyl)-4-aminomethyl-2-hydroxybenzamide
(172) N-(4-pyridyl)-4-(2-aminoethyl)benzamide
(173) N-(4-pyridyl)-4-aminomethyl-3-nitrobenzamide
(174) N-(4-pyridyl)-3-amino-4-aminomethylbenzamide
(175) (S)-(−)-N-(4-pyridyl)-4-(1-aminoethyl)benzamide
(176) (S)-(−)-N-(4-pyridyl)-2-(1-aminoethyl)benzamide
(177) (R)-(+)-N-(4-pyridyl)-4-(1-aminoethyl)-2-chlorobenzamide
(178) (R)-(+)-N-(1H-pyrrolo[2,3-b]pyridin-4-yl)-4-(1-(3-propylguanidino)ethyl)benzamide
(179) (R)-(−)-N-(1H-pyrrolo[2,3-b]pyridin-4-yl)-4-(1-aminoethyl)-3-azidebenzamide
(180) (R)-(+)-N-(4-pyridyl)-4-(1-aminoethyl)-2-nitrobenzamide
(181) (R)-(−)-N-(4-pyridyl)-4-(1-aminoethyl)-3-ethoxybenzamide
(182) (R)-(+)-N-(3-iodo-1H-pyrrolo[2,3-b]pyridin-4-yl)-4-(1-aminoethyl)benzamide
(183) (R)-(+)-N-(3-iodo-1H-pyrrolo[2,3-b]pyridin-4-yl)-4-(1-aminoethyl)-3-azidebenzamide
(184) (R)-(−)-N-(4-pyridyl)-4-(1-aminoethyl)-3-hydroxybenzamide
(185) N-(1H-pyrazolo[3,4-b]pyridin-4-yl)-4-guanidinomethyl-3-nitrobenzamide
(186) (R)-N-(1H-pyrazolo[3,4-b]pyridin-4-yl)-4-(1-guanidinoethyl)-3-nitrobenzamide
(187) (R)-N-(1H-pyrazolo[3,4-b]pyridin-4-yl)-4-(1-aminoethyl)-2-nitrobenzamide
(188) N-(1H-pyrazolo[3,4-b]pyridin-4-yl)-4-guanidinobenzamide
(189) (R)-N-(1H-pyrazolo[3,4-b]pyridin-4-yl)-4-(1-aminoethyl)-3-nitrobenzamide
(190) (R)-N-(1H-pyrazolo[3,4-b]pyridin-4-yl)-4-(1-guanidinoethyl)benzamide
(191) N-(1H-pyrazolo[3,4-b]pyridin-4-yl)-4-(1-amino-2-hydroxyethyl)benzamide
(192) N-(1H-pyrazolo[3,4-b]pyridin-4-yl)-4-aminomethyl-3-nitrobenzamide
(193) N-(1H-pyrrolo[2,3-b]pyridin-4-yl)-4-piperidinecarboxamide
(194) N-(1H-pyrazolo[3,4-b]pyridin-4-yl)-4-piperidinecarboxamide
(195) N-(1H-pyrazolo[3,4-b]pyridin-4-yl)-1-aminoacetyl-4-piperidinecarboxamide
(196) N-(1-methoxymethyl-1H-pyrazolo[3,4-b]pyridin-4-yl)-4-piperidinecarboxamide
(197) N-(2,3-dihydro-1H-pyrrolo[2,3-b]pyridin-4-yl)-4-piperidinecarboxamide
(198) N-(1H-pyrrolo[2,3-b]pyridin-4-yl)-1-(2-phenylethyl)-4-piperidinecarboxamide
(199) N-(1H-pyrrolo[2,3-b]pyridin-4-yl)-1-amidino-4-piperidinecarboxamide
(200) N-(1H-pyrrolo[2,3-b]pyridin-4-yl)-1-(3-phenylpropyl)-4-piperidinecarboxamide
(201) N-(1H-pyrrolo[2,3-b]pyridin-4-yl)-1-benzyl-4-piperidinecarboxamide
(202) N-(1H-pyrazolo[3,4-b]pyridin-4-yl)-1-(2-phenylethyl)-4-piperidinecarboxamide
(203) N-(1H-pyrazolo[3,4-b]pyridin-4-yl)-1-(3-phenylpropyl)-4-piperidinecarboxamide
(204) N-(1H-pyrrolo[2,3-b]pyridin-4-yl)-4-(1-amino-1-methylethyl)benzamide Preferred are compounds (80), (109), (110), (112), (115), (142), (143), (144), (145), (153), (157), (163), (165), (166) and (179).

The compound having a Rho kinase inhibitory activity may be a pharmaceutically acceptable acid addition salt, wherein the acid is exemplified by inorganic acid such as hydrochloric acid, hydrobromic acid, sulfuric acid and the like, and organic acid such as methanesulfonic acid, fumaric acid, maleic acid, mandelic acid, citric acid, tartaric acid, salicylic acid and the like. A compound having a carboxyl group can be converted to a salt with a metal such as sodium, potassium, calcium, magnesium, aluminum and the like, a salt with an amino acid such as lysine and the like. Further, monohydrate, dihydrate, ½ hydrate, ⅓ hydrate, ¼ hydrate, ⅔ hydrate, ³⁄₂ hydrate, ⅗ hydrate and the like are encompassed in the present invention.

The compound of the formula (I) can be synthesized by a method described in, for example, JP-A-62-89679, JP-A-3-218356, JP-A-5-194401, JP-A-6-41080, WO95/28387, WO98/06433 and the like.

When the above-mentioned compound having a Rho kinase inhibitory activity has an optical isomer, its racemate or cis-trans isomers, all of them can be used in the present invention. These isomers can be isolated by a conventional method or can be produced using starting materials of the isomers.

A compound having a Rho kinase inhibitory activity is used as a pharmaceutical agent, particularly, an antitumor effect potentiator or a pharmaceutical composition for reinforcing antitumor effect of the present invention, it is prepared as a general pharmaceutical preparation.

For example, the compound having a Rho kinase inhibitory activity is mixed with a pharmaceutically acceptable carrier (e.g., excipient, binder, disintegrator, corrective, corrigent, emulsifier, diluent, solubilizer and the like) to give a pharmaceutical composition or a pharmaceutical preparation in the form of tablet, pill, powder, granule, capsule, troche, syrup, liquid, emulsion, suspension, injection (e.g., liquid, suspension and the like), suppository, inhalant, percutaneous absorber, eye drop, eye ointment and the like in the form suitable for oral or parenteral preparation.

When preparing a solid preparation, additives such as sucrose, lactose, cellulose sugar, D-mannitol, maltitol, dextran, starches, agar, arginates, chitins, chitosans, pectines, tragacanth gum, gum arabic, gelatins, collagens, casein, albumin, calcium phosphate, sorbitol, glycine, carboxymethylcellulose, polyvinylpyrrolidone, hydroxypropylcellulose, hydroxypropylmethylcellulose, glycerol, polyethyleneglycol, sodium hydrogencarbonate, magnesium stearate, talc and the like are used. Tablets can be applied with a typical coating, where necessary, to give sugar coated tablets, enteric tablets, film-coated tablets, two-layer tablets and multi-layer tablets.

When preparing a semi-solid preparation, animal and plant fats and oils (e.g., olive oil, corn oil, castor oil and the like), mineral fats and oils (e.g., petrolatum, white petrolatum, solid paraffin and the like), wax (e.g., jojoba oil, carnauba wax, bee wax and the like), partly or entirely synthesized glycerol fatty acid esters (e.g., lauric acid, myristic acid, palmitic acid and the like), and the like are used. Examples of commercially available products of these include Witepsol (manufactured by Dynamitnovel Ltd.), Farmazol (manufactured by NOF Corporation) and the like.

When preparing a liquid preparation, an additive, such as sodium chloride, glucose, sorbitol, glycerol, olive oil, propylene glycol, ethyl alcohol and the like, is used. When preparing an injection, a sterile aqueous solution such as physiological saline, isotonic solution, oily solution (e.g., sesame oil and soybean oil) and the like are used. Where necessary, a suitable suspending agent such as sodium carboxymethylcellulose, nonionic surfactant, solubilizer (e.g., benzyl benzoate and benzyl alcohol), and the like can be concurrently used. Moreover, when an eye drop is prepared, an aqueous liquid or solution is used, which is particularly a sterile injectable aqueous solution. The eye drop can appropriately contain various additives such as buffer (borate buffer, acetate buffer, carbonate buffer and the like are preferable for reducing irritation), isotonicity agent, solubilizer, preservative, thickener, chelating agent, pH adjusting agent (generally, pH is preferably adjusted to about 6–8.5) and aromatic.

The dose of the active ingredient of these preparations, is 0.1–100 wt %, suitably 1–50 wt %, of the preparation. While the dose varies depending on the symptom, body weight, age and the like of patients, it is generally about 1–500 mg a day for an adult, which is administered once to several times a day.

An antitumor effect potentiator or a pharmaceutical composition for reinforcing antitumor effect containing a compound having a Rho kinase inhibitory activity of the present invention as an active ingredient can be administered by any method as long as it is in the form permitting concurrent use with an antitumor agent or a compound having an anti-tumor activity. For example, an antitumor agent is added to an antitumor effect potentiator or a pharmaceutical composition for reinforcing antitumor effect of the present invention and administered as a single composition. Alternatively, an antitumor agent and an antitumor effect potentiator or a pharmaceutical composition for reinforcing antitumor effect of the present invention may be formulated into preparations capable of separate administration and administered by different administration methods.

In the present invention, administration of an antitumor agent is essential to achieve the effect. The antitumor agent to be administered includes those mentioned above, and the administration method may be one generally employed in the field depending on the antitumor agent to be administered. The dose of the antitumor agent varies depending on the kind of the pharmaceutical agent to be administered, condition, body weight and age of patients, and the like, and determined based thereon. Inasmuch as the antitumor effect potentiator of the present invention is concurrently used in the present invention, the dose of the antitumor agent itself can be reduced as compared to a single administration. The timing of administration of the antitumor agent is appropriately determined depending on the kind of the pharmaceutical agent to be administered, symptoms, body weight and age of patients, and the like. The administration is preferably started at the same when the antitumor effect potentiator of the present invention is administered. The period of administration of the antitumor agent is also appropriately determined depending on the kind of the pharmaceutical agent to be administered, symptoms, body weight and age of patients, and the like.

EXAMPLES

The present invention is explained in detail by referring to formulation examples and pharmacological action. The present invention is not limited in any way by the examples.

In the following Formulation Examples and Experimental Examples, (R)-(+)-N-(4-pyridyl)-4-(1-aminoethyl) benzamide HCl, which is a compound having a Rho kinase inhibitory activity, was used.

In the following, the preparation method of the pharmaceutical agent of the present invention is explained by referring to Formulation Examples.

Formulation Example 1

Tablet

| | |
|---|---|
| Compound of the present invention | 10.0 mg |
| Lactose | 50.0 mg |
| Cornstarch | 20.0 mg |
| Crystalline cellulose | 29.7 mg |
| Polyvinylpyrrolidone K30 | 5.0 mg |
| Talc | 5.0 mg |
| Magnesium stearate | 0.3 mg |
| | 120.0 mg |

The compound of the present invention, lactose, cornstarch and crystalline cellulose were mixed, kneaded with polyvinylpyrrolidone K30 paste solution and passed through a 20-mesh sieve for granulation. After drying at 50° C. for 2 hours, the granules were passed through a 24-mesh sieve, and talc and magnesium stearate were added using a ϕ7 mm punch, tablets weighing 120 mg per tablet were prepared.

Formulation Example 2

Capsules

| | |
|---|---|
| Compound of the present invention | 10.0 mg |
| Lactose | 70.0 mg |
| Cornstarch | 35.0 mg |
| Polyvinylpyrrolidone K30 | 2.0 mg |
| Talc | 2.7 mg |
| Magnesium stearate | 0.3 mg |
| | 120.0 mg |

The compound of the present invention, lactose and cornstarch were mixed, kneaded with polyvinylpyrrolidone K30 paste solution and passed through a 20-mesh sieve for granulation. After drying at 50° C. for 2 hours, the granules were passed through a 24-mesh sieve and talc and magnesium stearate were added. The mixture was filled in a hard capsule (No. 4) to give a capsule weighing 120 mg.

Formulation Example 3

Injections

| | |
|---|---|
| Compound of the present invention | 5.0 mg |
| Sodium chloride | 18.0 mg |
| with distilled water for injection | |
| total amount | 2.0 ml |

Sodium chloride was dissolved in about 80 parts of distilled water for injection, and the compound of the present invention was added and dissolved to give a total amount of 100 parts. After filtering through a membrane filter (0.2 μm), it was filled in a 2 ml ampoule and sterilized at 115° C. for 30 min to give 2 ml injection.

In the following, the pharmacological action of the pharmaceutical agent of the present invention is explained by Experimental Examples.

Experimental Example 1

Suppression of cancer metastasis by a combination of the compound of the present invention and anticancer agents (cisplatin, etoposide and paclitaxel) in hematogenous pulmonary metastasis after transplantation of mouse B16-F10 melanoma cultured cells into tail vein (Method)

(1) Preparation of mouse B16-F10 melanoma cultured cells (hereinafter simply B16-F10)

B16-F10 cells (a permission to use was obtained from US M.D. Anderson Cancer Center, Dr. I. Fidler and provided for use from Japanese Foundation for cancer research·cancer chemotherapy center, Dr. Tsuruo) were subcultured in a Minimum Essential Medium: containing 0.225% sodium hydrogencarbonate, 2 mM L-glutamine, 1 mM non-essential amino acids, MEM vitamins, 1 mM pyruvic acid, hereinafter simply MEM, supplemented with 5% of heat inactivated fetal calf serum (FCS). For experiment, B16-F10 cells were suspended in MEM at $5 \times 10^5$ cells/mL and 0.2 mL thereof was transferred into the tail vein of 8-week-old male C57BL/6 mice (8 per group). At 14 days after the cell transfer, the mice were autopsied and the number of metastatic colonies of B16-F10 cells formed in both lungs was visually counted.

(2) The test compound (the compound of the present invention) was dissolved in 0.5% metolose solution and orally administered once a day for 14 days from the day of transplantation, or dissolved in physiological saline, filled in an osmotic pump (product name: Alzet, model 1002, flow rate 0.25 mL/h, for use for 14 days), and the osmotic pump was intraperitoneally transplanted into the mice one day before the transplantation of B16-F10 cells.

(3) As regards cisplatin, a preparation for injection (product name: Randa injection) was diluted with physiological saline and intraperitoneally administered once the day after transplantation of B16-F10 cells.

As regards etoposide, a preparation for injection (product name: Lastet injection) was diluted with physiological saline and repeatedly administered intraperitoneally once a day for 5 days starting from one day after transplantation of B16-F10 cells.

Paclitaxel was purchased from Sigma chemicals Co., suspended in 0.5% metolose solution and repeatedly administered intraperitoneally once every other day (3 times/week for 2 weeks) starting from one day after transplantation of B16-F10 cells.

(Results)

The number (average and standard error) of pulmonary metastatic colonies of B16-F10 cells was determined for each group and the results are summarized in Tables 1, 2, 4 and 5. In addition, the values of combination index (CI) of the action in concomitant use analyzed by Median Effect Analysis (References [1] and [2]) with regard to the combination group of the compound of the present invention and the anticancer agent are summarized in Table 3 and Table 6. In References [1] and [2], a CI value below 1 is explained to show a synergistic action and a CI value of 1 is explained to show an additive action.

TABLE 1

| cisplatin (mg/kg) | compound of the present invention (mg/kg) (oral administration) | T/C±standard error[1] (%) | significant difference[2] |
|---|---|---|---|
| 0.5 | 0 | 80.2 ± 13.2 | |
| 1 | 0 | 66.5 ± 8.3 | |
| 2.5 | 0 | 57.5 ± 3.0 | |
| 5 | 0 | 53.3 ± 4.5 | |
| 10 | 0 | 46.7 ± 4.1 | |
| 0 | 1 | 77.1 ± 10.0 | |

TABLE 1-continued

| cisplatin (mg/kg) | compound of the present invention (mg/kg) (oral administration) | T/C±standard error[1] (%) | significant difference[2] |
|---|---|---|---|
| 0 | 3 | 65.2 ± 3.7 | |
| 5 | 1 | 13.4 ± 1.4 | |
| 5 | 3 | 14.4 ± 2.0 | |
| 10 | 1 | 19.5 ± 3.0 | p < 0.01 |
| 10 | 3 | 16.5 ± 1.4 | p < 0.01 |

[1]T/C = average number of pulmonary metastatic colonies of administration group/average number of pulmonary metastatic colonies of control group ×100 (%)
[2]combination group vs. cisplatin (10 mg/kg) alone administration group, n = 8, Dunnett's test

TABLE 2

| cisplatin (mg/kg) | compound of the present invention (mg/kg) (osmotic pump) | T/C±standard error[1] (%) | significant difference[2] |
|---|---|---|---|
| 0.5 | 0 | 81.7 ± 13.4 | |
| 1 | 0 | 67.7 ± 8.4 | |
| 2.5 | 0 | 58.6 ± 3.0 | |
| 5 | 0 | 54.3 ± 4.6 | |
| 10 | 0 | 30.8 ± 4.7 | |
| 0 | 0.3 | 73.4 ± 10.1 | |
| 0 | 1 | 69.9 ± 7.7 | |
| 0 | 3 | 63.5 ± 7.7 | |
| 10 | 0.3 | 12.1 ± 2.1 | |
| 10 | 1 | 13.0 ± 1.8 | |
| 10 | 3 | 11.1 ± 1.4 | P < 0.05 |

[1]T/C = average number of pulmonary metastatic colonies of administration group/average number of pulmonary metastatic colonies of control group ×100 (%)
[2]combination group vs. cisplatin (10 mg/kg) alone administration group, n = 8, Dunnett's test As is clear from Tables 1 and 2, the number of pulmonary metastatic colonies of B16-F10 cells was found to have significantly decreased in the combination group of the compound of the present invention and cisplatin as compared to the cisplatin alone administration group ($p<0.01$ or $p<0.05$, Dunnett's test).

The CI value was determined in the same manner with regard to the combination group of the compound of the present invention and cisplatin. The values are summarized in Table 3.

TABLE 3

| cisplatin (mg/kg) | compound of the present invention (mg/kg) | CI (Combination Index) | |
|---|---|---|---|
| | | oral administration | osmotic pump |
| 10 | 0.3 | | 0.19 |
| 10 | 1 | 0.12 | 0.21 |
| 10 | 3 | 0.09 | 0.17 |

As shown in Table 3, the CI value of the action in concomitant use when the compound of the present invention and cisplatin were used in combination was lower than 1 for every dose. Therefrom it was suggested that the compound of the present invention when used with cisplatin in combination synergistically suppressed hematogenous pulmonary metastasis of B16-F10 cells.

The results of the compound of the present invention and etoposide or paclitaxel used in combination are summarized in Table 4 and Table 5, respectively.

TABLE 4

| etoposide (mg/kg) | compound of the present invention (mg/kg) (oral administration) | T/C±standard error[1] (%) | significant difference[2] |
|---|---|---|---|
| 1 | 0 | 56.0 ± 3.0 | |
| 2.5 | 0 | 34.0 ± 7.4 | |
| 5 | 0 | 33.4 ± 4.0 | |
| 10 | 0 | 22.5 ± 4.2 | |
| 25 | 0 | 14.5 ± 2.6 | |
| 0 | 1 | 83.4 ± 10.8 | |
| 0 | 3 | 70.5 ± 4.0 | |
| 5 | 1 | 22.0 ± 4.8 | P < 0.05 |
| 5 | 3 | 19.2 ± 2.8 | P < 0.01 |

[1]T/C = average number of pulmonary metastatic colonies of administration group/average number of pulmonary metastatic colonies of control group ×100 (%)
[2]combination group vs. etoposide (5 mg/kg) alone administration group, n = 8, Dunnett's test

TABLE 5

| paclitaxel (mg/kg) | compound of the present invention (mg/kg) (oral administration) | T/C±standard error[1] (%) | significant difference[2] |
|---|---|---|---|
| 1 | 0 | 75.9 ± 5.9 | |
| 2.5 | 0 | 48.8 ± 8.4 | |
| 5 | 0 | 37.3 ± 4.0 | |
| 10 | 0 | 30.3 ± 3.6 | |
| 25 | 0 | 31.5 ± 7.2 | |
| 0 | 1 | 69.8 ± 9.0 | |
| 0 | 3 | 59.0 ± 3.3 | |
| 5 | 1 | 20.6 ± 2.6 | P < 0.05 |
| 5 | 3 | 16.3 ± 3.0 | P < 0.01 |

[1]T/C = average number of pulmonary metastatic colonies of administration group/average number of pulmonary metastatic colonies of control group ×100 (%)
[2]combination group vs. paclitaxel (5 mg/kg) alone administration group, n = 8, Dunnett's test As is clear from Tables 4 and 5, the number of pulmonary metastatic colonies of B16-F10 cells was found to have significantly decreased in the combination group of the present invention and etoposide or paclitaxel as compared to the etoposide or paclitaxel alone administration group ($p<0.01$ or $p<0.05$ Dunnett's test).

The CI value was determined in the same manner with regard to the combination group of the compound of the present invention and etoposide or paclitaxel. The results are summarized in Table 6.

TABLE 6

| compound of the present invention | CI (Combination Index) | |
|---|---|---|
| (mg/kg) (oral) | Etoposide (5 mg/kg) | Paclitaxel (5 mg/kg) |
| 1 | 0.42 | 0.63 |
| 3 | 0.34 | 0.34 |

As shown in Table 6, the combination index of the action in concomitant use when the compound of the present invention and etoposide or paclitaxel were used in combination was lower than 1 for both combinations. Therefrom it was suggested that the compound of the present invention when used with etoposide or paclitaxel in combination synergistically suppressed hematogenous pulmonary metastasis of B16-F10 cells.

In the experiments of Tables 1, 2, 4 and 5, the number of pulmonary metastatic colonies of the control group was 164.2–232.6 on average.

Example 2

Measurement Method of Cell Growth Activity (Method)

Mouse melanoma B16-F10 cells (the aforementioned) were cultured in MEM supplemented with 2 mM L-glutamine, 1 mM MEM non-essential amino acids, 1% MEM vitamins, 1 mM pyruvic acid and 5% FCS, and the cells were scraped off from the culture flask every 3–4 days with a cell scraper (No. 3010, manufactured by Coaster), diluted 10-fold and maintained by subculture. In the experiment examining the effect of the test substance on the cell growth, the B16-F10 cells maintained in vitro by subculture were recovered with a cell scraper, suspended in MEM supplemented with 10% FCS at $2 \times 10^5$ cells/mL and added to a 96 well microtest plate (Becton Dickinson) at $1 \times 10^4$ cells/50 μL/well. Furthermore, 50 μL of a test substance at a 2-fold concentration of the final concentration was added to the well, and cultured in a $CO_2$ incubator (MCO-175, SANYO Electric Co., Ltd.) at 37° C., 5% $CO_2$ 95% air for 72 hr.

After culture, 10 mg/mL of MTT [(3-[4,5-Dimethylthiazol-2-yl]-2,5-diphenyl-tetrazolium bromide)] was added at 10 μL/well, which was followed by culture for 3 hr. Thereafter, 100 μL of 10% SDS (sodium dodecylsulfate)—0.01N HCl was added to dissolve the pigment and absorbance at 570 nm was measured with a multilabel counter (1420 ARVO SX, Pharmacia Biotech Corporation). According to the concentration of the test substance, each well was expressed by absorbance, and average value and standard error. Using the well, to which the medium alone was added, as a control, the growth inhibition rate was calculated according to the following formula.

$$\text{growth inhibition rate } (\%) = \left(1 - \frac{OD_{570} \text{ of well added with test substance}}{OD_{570} \text{ of well added with medium alone}}\right) \times 100$$

Analysis method: Based on the dose reaction curves of the inventive compound alone treatment group and cisplatin alone treatment group, the combination index (CI) of the action in concomitant use is calculated by median effect analysis (References [1] and [2]).

(Results)

The effects of cisplatin and the compound of the present invention on in vitro growth of mouse melanoma B16-F10 cells is shown in Table 7.

TABLE 7

| cisplatin (μM) | compound of the present invention | average growth suppression rate ± standard error (%) | significant difference |
|---|---|---|---|
| 10 | 0 | 5.813 ± 1.510 | |
| 30 | 0 | 29.609 ± 4.503 | |
| 100 | 0 | 96.631 ± 0.109 | |
| 0 | 0.1 | 4.389 ± 3.094 | |
| 0 | 0.3 | 5.196 ± 0.214 | |
| 0 | 1 | 7.877 ± 0.727 | |
| 0 | 3 | 10.012 ± 1.459 | |

TABLE 7-continued

| cisplatin (μM) | compound of the present invention | average growth suppression rate ± standard error (%) | significant difference |
|---|---|---|---|
| 0 | 10 | 10.700 ± 0.365 | |
| 0 | 30 | 22.657 ± 4.784 | |
| 0 | 100 | 57.960 ± 8.575 | |
| 10 | 0.3 | 17.200 ± 11.245 | NS (p = 0.1293) |
| 10 | 1 | 17.319 ± 4.397 | NS (P = 0.1236) |
| 10 | 3 | 26.406 ± 8.364 | p = 0.0028 |
| 10 | 10 | 43.796 ± 5.446 | p = 0.0000 |
| 10 | 30 | 90.320 ± 2.220 | p = 0.0000 |
| 10 | 100 | 96.180 ± 0.164 | p = 0.0000 |

[1])combination group vs. cisplatin (10 μM) alone administration group, Dunnett's test Moreover, the results of the combination use of the compound of the present invention and cisplatin in CI value is shown in Table 8.

TABLE 8

| cisplatin (μM) | compound of the present invention (μM) | CI (Combination index) |
|---|---|---|
| 10 | 0.3 | 0.42929 |
| 10 | 1 | 0.46563 |
| 10 | 3 | 0.44781 |
| 10 | 10 | 0.44029 |
| 10 | 30 | 0.50708 |
| 10 | 100 | 0.35585 |

References

1) B. D. Kahan. Concentration-controlled immunosuppressive regimens using cyclosporine with sirolimus or brequinar in human renal transplantation. Transplant. Proc., 27, 33–36, 1995.

2) K. Watanabe, S. Ito, K. Kikuchi, N. Ichikawa, Y. Ando, K. Meigata, Y. Nomura, T. Degawa, Y. Beck, S. Tomikawa, T. Nagao, and H. Uchida. Synergistic effect of tacrolimus and mizoribine on in vitro and in vivo experiments assessed by a combination index. Jap. J. Transplant., 31, 23–30, 1996.

INDUSTRIAL APPLICABILITY

From the above-mentioned Formulation Examples and Experimental Examples and other pharmacological experiments, a compound having a Rho kinase inhibitory activity reinforces an antitumor effect of an antitumor agent and is useful as an antitumor effect potentiator.

Particularly, from the above-mentioned Experimental Examples, a compound having a Rho kinase inhibitory activity remarkably potentiates the antitumor effect of cisplatin. Therefore, a compound having a Rho kinase inhibitory activity of the present invention can reduce the dose of an antitumor agent when combined with the antitumor agent, which in turn affords a sufficient effect and/or reduction of side effect.

This application is based on a patent application No. 190233/2000 filed in Japan, the contents of which are hereby incorporated by reference.

What is claimed is:

1. A pharmaceutical composition comprising an antitumor agent and an antitumor effect potentiator comprising a compound having a Rho kinase inhibitory activity as an active ingredient, which reinforces an antitumor effect of the antitumor agent, wherein the compound is an amide compound of the following formula (I)

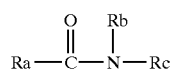
(I)

wherein

Ra is a group of the formula

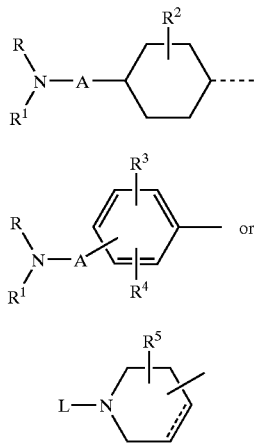

in the formulas (a) and (b),

R is hydrogen, alkyl, or cycloalkyl, cycloalkylalkyl, phenyl or aralkyl, which optionally has a substituent on the ring, or a group of the formula

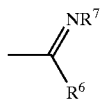
(d)

wherein $R^6$ is hydrogen, alkyl or formula: $-NR^8R^9$ wherein $R^8$ and $R^9$ are the same or different and each is hydrogen, alkyl, aralkyl or phenyl, $R^7$ is hydrogen, alkyl, aralkyl, phenyl, nitro or cyano, or $R^6$ and $R^7$ in combination show a group forming a heterocycle optionally further having, in the ring, oxygen atom, sulfur atom or optionally substituted nitrogen atom, $R^1$ is hydrogen, alkyl, or cycloalkyl, cycloalkylalkyl, phenyl or aralkyl, which optionally has a substituent on the ring, or R and $R^1$ in combination form, together with the adjacent nitrogen atom, a group forming a heterocycle optionally further having, in the ring, oxygen atom, sulfur atom or optionally substituted nitrogen atom, $R^2$ is hydrogen or alkyl, $R^3$ and $R^4$ are the same or different and each is hydrogen, alkyl, aralkyl, halogen, nitro, amino, alkylamino, acylamino, hydroxy, alkoxy, aralkyloxy, cyano, acyl, mercapto, alkylthio, aralkylthio, carboxy, alkoxycarbonyl, carbamoyl, mono- or dialkylcarbamoyl or azide, and A is a group of the formula

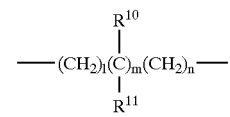
(e)

wherein $R^{10}$ and $R^{11}$ are the same or different and each is hydrogen, alkyl, haloalkyl, aralkyl, hydroxyalkyl, carboxy or alkoxycarbonyl, or $R^{10}$ and $R^{11}$ show a group which forms cycloalkyl in combination and l, m and n are each 0 or an integer of 1–3, in the formula (c), L is hydrogen, alkyl, aminoalkyl, mono- or dialkylaminoalkyl, tetrahydrofurfuryl, carbamoylalkyl, phthalimidoalkyl, amidino or a group of the formula

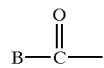
(f)

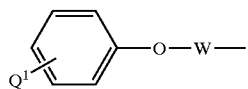
(g)

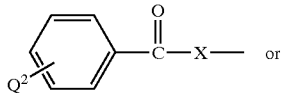
(h)

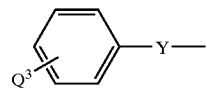
(i)

wherein B is hydrogen, alkyl, alkoxy, aralkyl, aralkyloxy, aminoalkyl, hydroxyalkyl, alkanoyloxyalkyl, alkoxycarbonylalkyl, α-aminobenzyl, furyl, pyridyl, phenyl, phenylamino, styryl or imidazopyridyl, $Q^1$ is hydrogen, halogen, hydroxy, aralkyloxy or thienylmethyl, W is alkylene, $Q^2$ is hydrogen, halogen, hydroxy or aralkyloxy, X is alkylene, $Q^3$ is hydrogen, halogen, hydroxy, alkoxy, nitro, amino, 2,3-dihydrofuryl or 5-methyl-3-oxo-2,3,4,5-tetrahydropyridazin-6-yl;

and Y is a single bond, alkylene or alkenylene, and in the formula (c), a broken line is a single bond or a double bond, and $R^5$ is hydrogen, hydroxy, alkoxy, alkoxycarbonyloxy, alkanoyloxy or aralkyloxycarbonyloxy;

Rb is a hydrogen, an alkyl, an aralkyl, an aminoalkyl or a mono- or dialkylaminoalkyl; and Rc is an optionally substituted heterocycle containing nitrogen, an isomer thereof and/or a pharmaceutically acceptable acid addition salt thereof.

2. The pharmaceutical composition of claim 1, wherein the compound having a Rho kinase inhibitory activity is an amide compound of the following formula (I')

(I')

wherein

Ra' is a group of the formula

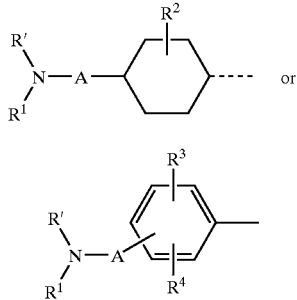

wherein

R' is hydrogen, alkyl, or cycloalkyl, cycloalkylalkyl, phenyl or aralkyl, which optionally has a substituent on the ring, $R^1$ is hydrogen, alkyl, or cycloalkyl, cycloalkylalkyl, phenyl or aralkyl, which optionally has a substituent on the ring, or R' and R1 in combination form, together with the adjacent nitrogen atom, a group forming a heterocycle optionally further having, in the ring, oxygen atom, sulfur atom or optionally substituted nitrogen atom, $R^2$ is hydrogen or alkyl, $R^3$ and $R^4$ are the same or different and each is hydrogen, alkyl, aralkyl, halogen, nitro, amino, alkylamino, acylamino, hydroxy, alkoxy, aralkyloxy, cyano, acyl, mercapto, alkylthio, aralkythio, carboxy, alkoxycarbonyl, carbamoyl, mono- or dialkylcarbamoyl or azide, and A is a group of the formula

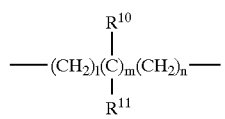

wherein $R^{10}$ and $R^{11}$ are the same or different and each is hydrogen, alkyl, haloalkyl, aralkyl, hydroxyalkyl, carboxy or alkoxycarbonyl, or $R^{10}$ and $R^{11}$ show a group which forms cycloalkyl in combination and l, m and n are each 0 or an integer of 1–3, Rb is a hydrogen, an alkyl, an aralkyl, an aminoalkyl or a mono- or dialkylaminoalkyl; and Rc is an optionally substituted heterocycle containing nitrogen, an isomer thereof and/or a pharmaceutically acceptable acid addition salt thereof.

3. A method of treating a tumor, which comprises administering a pharmaceutically effective amount of a compound having a Rho kinase inhibitory activity and a pharmaceutically effective amount of an antitumor agent to a patient, wherein the compound having a Rho kinase inhibitory activity is an amide compound of the following formula (I)

(I)

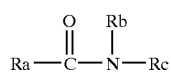

wherein

Ra is a group of the formula

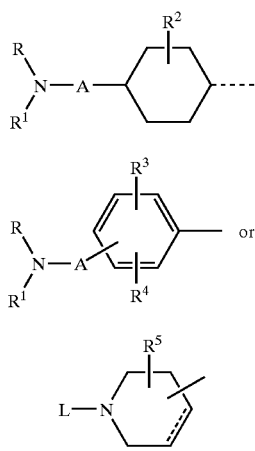

in the formulas (a) and (b),

R is hydrogen, alkyl, or cycloalkyl, cycloalkylalkyl, phenyl or aralkyl, which optionally has a substituent on the ring, or a group of the formula (d)

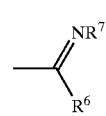

wherein $R^6$ is hydrogen, alkyl or formula: —$NR^8R^9$ wherein $R^8$ and $R^9$ are the same or different and each is hydrogen, alkyl, aralkyl or phenyl, $R^7$ is hydrogen, alkyl, aralkyl, phenyl, nitro or cyano, or $R^6$ and $R^7$ in combination show a group forming a heterocycle optionally further having, in the ring, oxygen atom, sulfur atom or optionally substituted nitrogen atom, $R^1$ is hydrogen, alkyl, or cycloalkyl, cycloalkylalkyl, phenyl or aralkyl, which optionally has a substituent on the ring, or R and $R^1$ in combination form, together with the adjacent nitrogen atom, a group forming a heterocycle optionally further having, in the ring, oxygen atom, sulfur atom or optionally substituted nitrogen atom, $R^2$ is hydrogen or alkyl, $R^3$ and $R^4$ are the same or different and each is hydrogen, alkyl, aralkyl, halogen, nitro, amino, alkylamino, acylamino, hydroxy, alkoxy, aralkyloxy, cyano, acyl, mercapto, alkylthio, aralkylthio, carboxy, alkoxycarbonyl, carbamoyl, mono- or dialkylcarbamoyl or azide, and A is a group of the formula

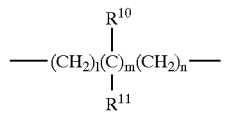

wherein $R^{10}$ and $R^{11}$ are the same or different and each is hydrogen, alkyl, haloalkyl, aralkyl, hydroxyalkyl, carboxy or alkoxycarbonyl, or $R^{10}$ and $R^{11}$ show a group which forms cycloalkyl in combination and l, m and n are each 0 or an integer of 1–3, in the formula (c), L is hydrogen, alkyl, aminoalkyl, mono- or dialkylaminoalkyl, tetrahydrofurfuryl, carbamoylalkyl, phthalimidoalkyl, amidino or a group of the formula

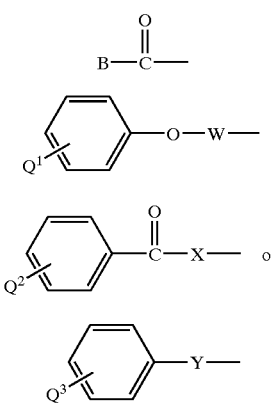

wherein B is hydrogen, alkyl, alkoxy, aralkyl, aralkyloxy, aminoalkyl, hydroxyalkyl, alkanoyloxyalkyl, alkoxycarbonylalkyl, α-aminobenzyl, furyl, pyridyl, phenyl, phenylamino, styryl or imidazopyridyl, $Q^1$ is hydrogen, halogen, hydroxy, aralkyloxy or thienylmethyl, W is alkylene, $Q^2$ is hydrogen, halogen, hydroxy or aralkyloxy, X is alkylene, $Q^3$ is hydrogen, halogen, hydroxy, alkoxy, nitro, amino, 2,3-dihydrofuryl or 5-methyl-3-oxo-2,3,4,5-tetrahydropyridazin-6-yl;

and Y is a single bond, alkylene or alkenylene, and in the formula (c), a broken line is a single bond or a double bond, and $R^5$ is hydrogen, hydroxy, alkoxy, alkoxycarbonyloxy, alkanoyloxy or aralkyloxycarbonyloxy;

Rb is a hydrogen, an alkyl, an aralkyl, an aminoalkyl or a mono- or dialkylaminoalkyl; and Rc is an optionally substituted heterocycle containing nitrogen, an isomer thereof and/or a pharmaceutically acceptable acid addition salt thereof.

4. The method of claim 3, wherein the compound having a Rho kinase inhibitory activity is an amide compound of the formula (I'), an isomer thereof and/or a pharmaceutically acceptable acid addition salt thereof, wherein the compound having a Rho kinase inhibitory activity is an amide compound of the following formula (I')

wherein

Ra' is a group of the formula

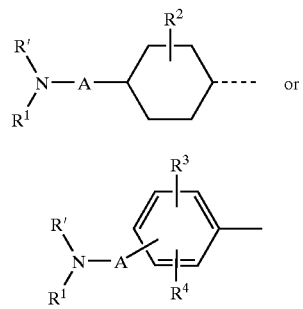

wherein

R' is hydrogen, alkyl, or cycloalkyl, cycloalkylalkyl, phenyl or aralkyl, which optionally has a substituent on the ring, $R^1$ is hydrogen, alkyl, or cycloalkyl, cyoloalkylalkyl, phenyl or aralkyl, which optionally has a substituent on the ring, or R' and $R^1$ in combination form, together with the adjacent nitrogen atom, a group forming a heterocycle optionally further having, in the ring, oxygen atom, sulfur atom or optionally substituted nitrogen atom, $R^2$ is hydrogen or alkyl, $R^3$ and $R^4$ are the same or different and each is hydrogen, alkyl, aralkyl, halogen, nitro, amino, alkylamino, acylamino, hydroxy, alkoxy, aralkyloxy, cyano, acyl, mercapto, alkylthio, aralkylthio, carboxy, alkoxycarbonyl, carbamoyl, mono- or dialkylcarbamoyl or azide, and A is a group of the formula

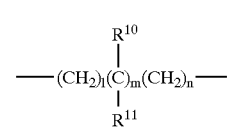

wherein $R^{10}$ and $R^{11}$ are the same or different and each is hydrogen, alkyl, haloalkyl, aralkyl, hydroxyalkyl, carboxy or alkoxycarbonyl, or $R^{10}$ and $R^{11}$ show a group which forms cyoloalkyl in combination and l, m and n are each 0 or an integer of 1–3, Rb is a hydrogen, an alkyl, an aralkyl, an aminoalkyl or a mono- or dialkylaminoalkyl; and Rc is an optionally substituted heterocycle containing nitrogen, an isomer thereof and/or a pharmaceutically acceptable acid addition salt thereof.

5. The method of claim 3, wherein the compound having a Rho kinase inhibitory activity is a compound selected from the group consisting of (+)-trans-4-(1-aminoethyl)-1-(4-pyridylcarbamoyl)cyclohexane, (+)-trans-N-(1H-pyrrolo[2,3-b]pyridin-4-yl)-4-(1-aminoethyl)cyclohexanecarboxamide, (R)-(+)-N-(4-pyridyl)-4-(1-aminoethyl)

benzamide and (R)-(+)-N-(1H-pyrrolo[2,3-b]pyridin-4-yl)-4-(1-aminoethyl)benzamide, and/or a pharmaceutically acceptable acid addition salt thereof.

6. The method of claim 3, wherein the compound having a Rho kinase inhibitory activity is (R)-(+)-N-(4-pyridyl)-4-(1-aminoethyl)benzamide and/or a pharmaceutically acceptable acid addition salt thereof.

7. The method of claim 3, wherein the antitumor agent is selected from cisplatin, etoposide and paclitaxel.

8. The method of claim 7, wherein the antitumor agent is cisplatin.

9. The method of claim 3, wherein the antitumor agent is selected from cisplatin, etoposide and paclitaxel.

10. The method of claim 9, wherein the antitumor agent is cisplatin.

* * * * *